United States Patent
Cheng

(10) Patent No.: US 10,689,484 B2
(45) Date of Patent: *Jun. 23, 2020

(54) METHOD FOR ELECTROPOLYMERIZATION OF HYDROPHILIC EDOT MONOMERS IN AN AQUEOUS SOLUTION

(71) Applicant: THE UNIVERSITY OF AKRON, Akron, OH (US)

(72) Inventor: Gang Cheng, Wilmette, IL (US)

(73) Assignee: THE UNIVERSITY OF AKRON, Akron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/764,049

(22) PCT Filed: Sep. 28, 2016

(86) PCT No.: PCT/US2016/054111
§ 371 (c)(1),
(2) Date: Mar. 28, 2018

(87) PCT Pub. No.: WO2017/058871
PCT Pub. Date: Apr. 6, 2017

(65) Prior Publication Data
US 2018/0282472 A1    Oct. 4, 2018

Related U.S. Application Data

(60) Provisional application No. 62/233,708, filed on Sep. 28, 2015.

(51) Int. Cl.
C08G 61/12    (2006.01)
A61L 31/10    (2006.01)
(Continued)

(52) U.S. Cl.
CPC ............ C08G 61/126 (2013.01); A61L 31/10 (2013.01); C09D 5/24 (2013.01); C09D 165/00 (2013.01);
(Continued)

(58) Field of Classification Search
CPC .. C08G 61/123; C08G 61/124; C08G 61/125; C08G 61/126; C08G 2261/143; C08G 2261/3223; C08G 2261/94
See application file for complete search history.

(56) References Cited

U.S. PATENT DOCUMENTS 6,856,840 B2    2/2005 Munshi
2013/0029268 A1    1/2013 Koyama et al.
(Continued)

FOREIGN PATENT DOCUMENTS

WO    2015/031265 A1    3/2015
WO    2015/054484 A1    4/2015

OTHER PUBLICATIONS

Cao, B. et al., Integrated zwitterionic conjugated poly(carboxybetaine thiophene) as a new biomaterial platform. Chemical Science, vol. 6, 2015, published online Sep. 30, 2014, pp. 782-788.
(Continued)

*Primary Examiner* — Shane Fang
(74) *Attorney, Agent, or Firm* — Renner Kenner Greive Bobak Taylor & Weber

(57) ABSTRACT

In one or more embodiments, the present invention provides a method of forming compact, flexible, stable and biocompatible conducting polymer coating for bioelectronics devices. In one or more embodiments, the present invention relates to a novel method of synthesizing a sulfobetaine-functionalized conjugated polymer platform using 3,4-ethylenedioxythiophene (EDOT) as the conducting backbone (SBEDOT). This SBEDOT monomer is highly water-
(Continued)

soluble and can be directly polymerized to form a densely packed film/coating on conductive or semi-conductive surfaces through electro-polymerization in a 100% aqueous solution without the need for organic solvents or surfactants. These polySBEDOT (PSBEDOT) coated surfaces have been shown to have electro-switchable antimicrobial/antifouling properties and excellent electrically conducting properties, which minimize infection, increase biocompatibility, and improve the performance of bioelectronics.

18 Claims, 10 Drawing Sheets

(51) Int. Cl.
    *C09D 5/24*     (2006.01)
    *C09D 165/00*     (2006.01)
    *C25D 9/02*     (2006.01)
    *H01L 51/00*     (2006.01)
    *H01L 51/42*     (2006.01)

(52) U.S. Cl.
    CPC ............ C25D 9/02 (2013.01); H01L 51/0037 (2013.01); *A61L 2400/18* (2013.01); *A61L 2420/02* (2013.01); *C08G 2261/143* (2013.01); *C08G 2261/1424* (2013.01); *C08G 2261/1452* (2013.01); *C08G 2261/18* (2013.01); *C08G 2261/3223* (2013.01); *C08G 2261/44* (2013.01); *C08G 2261/51* (2013.01); *C08G 2261/94* (2013.01); *H01L 51/42* (2013.01)

(56) References Cited

U.S. PATENT DOCUMENTS

2015/0068028 A1    3/2015   Hanssen et al.
2015/0337061 A1*  11/2015  Yano .................... C08F 134/04
                                                 427/58

OTHER PUBLICATIONS

Benesch, J. et al., Protein adsorption to oligo(ethylene glycol) self-assembled monolayers: Experiments with fibrinogen, heparinized plasma, and serum. Journal of Biomaterial Science, Polymer Edition, vol. 12, No. 6, 2001, pp. 581-597.

* cited by examiner

FIG. 11B [Figure S5-(new S6)-Right]

METHOD FOR ELECTROPOLYMERIZATION OF HYDROPHILIC EDOT MONOMERS IN AN AQUEOUS SOLUTION

CROSS REFERENCE TO RELATED APPLICATIONS

This application claims the benefit of U.S. provisional patent application Ser. No. 62/233,708 entitled "Electroactive Zwitterionic Poly(sulfobetaine 3,4-ethylenedioxythiophene) (PSBEDOT) with Controllable Properties for Bioelectronics," filed Sep. 28, 2015, and incorporated herein by reference in its entirety.

STATEMENT REGARDING FEDERALLY SPONSORED RESEARCH OR DEVELOPMENT SUPPORT

This invention was made with government support under contracts ECCS-1200032 and DMR-1454837 awarded by the National Science Foundation (NSF). The government has certain rights in the invention.

FIELD OF THE INVENTION

One or more embodiments of the present invention relates to a method for forming a zwitterionic conjugated polymer surface. In certain embodiments, the present invention relates to methods for electro-polymerization of hydrophilic EDOT monomers in an aqueous solution to form a zwitterionic conjugated polymer surface.

BACKGROUND OF THE INVENTION

Conjugated polymers (CP) hold great promises for next-generation bioelectronics, because of their good compatibility to biological systems, flexibility to fabrication and relatively low costs. Previous studies found that conjugated polymers could improve communications between electrochemical devices and biological systems initially; however, conjugated polymers, such as polyacetylene (PA), polyaniline (PANi), polypyrrole (PPy), polythiophene (PTh) and poly(3,4-thylenedioxythiophene) (PEDOT), are not originally designed for complex biological applications. When these synthetic polymers are used in biological systems, one major challenge is to keep a "clean" and biocompatible biotic-abiotic interface to minimize the foreign body reaction, reduce the infection, prolong the service life of the device, while maintaining materials' conductivity, stability and functionalities. The conventional conjugated polymers consist of hydrophobic or charged side chains. Biomolecules, mammalian cells and bacteria tend to attach to charged or hydrophobic surfaces. The adsorption of biomolecules and attachment of unwanted cells will reduce the sensitivity or lead to the failure of the embedded devices. To increase their biocompatibility, PTh, PANi and PPy hydrogels have been developed to combine the electrical properties from conjugated polymers with the properties of hydrogels. To gain the biocompatiblity, conducting polymers are blended or physically crosslinked with biocompatible and non-conducting polymers. For example, polyethylene glycol (PEG) was used to crosslink PANi for glucose sensing. However, non-conducting components compromise electrochemical properties of conducting materials. Furthermore, non-conducting components of current conducting hydrogels are not effective enough to prevent long-term biofouling and foreign body response. Previous study discovered that zwitterionic polymers could effectively resist nonspecific protein adsorption and cell attachment. In a previous study, an integrated poly(carboxybetaine thiophene) (PCBTh) both conducting and antifouling properties was developed. Due to the loosely packed polymer networks in these hydrogels, however, the electron conductivity of these materials are not yet suitable for applications that demand high electron/current transport.

It should be pointed out that much effort has been devoted to develop flexible, stable and biocompatible conducting polymers for CP based bioelectronic devices, but the starting materials used to form these conducting polymers are either poorly water-soluble or need the addition of surfactants to improve the aqueous processability. What is needed in the art is a method of forming flexible, stable and biocompatible conducting polymer coatings for bioelectronics devices that uses a monomer is that is highly water-soluble and can be directly polymerized in aqueous solution without using organic solvents or surfactants, while at the same time, maintaining electro-switchable antimicrobial/antifouling properties, excellent electrical conducting properties, increased biocompatibility, and improved bioelectronic performance.

SUMMARY OF THE INVENTION

In one or more embodiments, the present invention provide a method of forming flexible, stable and biocompatible conducting polymer coatings for bioelectronics devices that uses a monomer is that is highly water-soluble and can be directly polymerized in aqueous solution without using organic solvents or surfactants, which are incompatible with most bioelectronics applications, and maintain electro-switchable antimicrobial/antifouling properties, excellent electrical conducting properties, increased biocompatibility, and improved bioelectronic performance. In various embodiments, the present invention relates to novel methods of synthesizing a tightly packed sulfobetaine-functionalized conjugated polymer film or coating (SBEDOT) using 3,4-ethylenedioxythiophene (EDOT) as the conducting backbone. As will be appreciated by those of skill in the art, EDOT-based polymers have attracted significant research interests, for their exceptional conductivity, low oxidation potential, relatively high chemical and thermal stability and special optical properties. The SBEDOT monomers used in various embodiments of the present invention are highly water-soluble and can be directly polymerized to form a densely packed film/coating on a conductive or semi-conductive surface through electro-polymerization in a 100% aqueous solution without organic solvents or surfactants. These polySBEDOT (PSBEDOT) coated surfaces have been shown to have electro-switchable antimicrobial/antifouling properties, excellent electrically conducting properties to minimize infection, increased biocompatibility and to improve the performance of bioelectronics.

In a first aspect, the present invention is directed to a method of forming a polymer film or coating on a substrate from an aqueous solution of one or more hydrophilic EDOT-derived monomer(s) comprising: selecting a suitable substrate, the substrate having a conductive or semiconductive surface; preparing a hydrophilic EDOT monomer comprising a terminal EDOT group and a betaine group; dissolving the hydrophilic EDOT monomer in water or an aqueous solution; placing the substrate in the solution so that the solution is in contact with the surface of the substrate;

applying an electric current to the solution, thereby causing the hydrophilic EDOT monomer to polymerize on the surface of the substrate.

In one or more embodiment, the substrate is selected from the group consisting of implantable medical devices, steel, stainless steel, titanium, titanium alloys, silicon, and/or ITO coated substrates, gold coated substrates, aluminum, aluminum alloys, platinum, noble metals, noble metals, and combinations thereof. In one or more embodiments, the method of forming a polymer film or coating on a substrate from an aqueous solution of one or more hydrophilic EDOT-derived monomer(s) of the present invention includes any one or more of the above referenced embodiments of the first aspect of the present invention wherein the conductive or semiconductive surface comprises a conductive or semiconductive material selected from the group consisting of steel, stainless steel, titanium, titanium alloys, aluminum, aluminum alloys, silicon, iridium tin oxide (ITO), gold, platinum, noble metals and alloys and combinations thereof.

In one or more embodiments, the method of forming a polymer film or coating on a substrate from an aqueous solution of one or more hydrophilic EDOT-derived monomer(s) of the present invention includes any one or more of the above referenced embodiments of the first aspect of the present invention wherein the betaine group is a sulfobetaine. In one or more embodiments, the method of forming a polymer film or coating on a substrate from an aqueous solution of one or more hydrophilic EDOT-derived monomer(s) of the present invention includes any one or more of the above referenced embodiments of the first aspect of the present invention wherein the hydrophilic EDOT monomer is 3-(((2,3-dihydrothieno[3,4-b][1,4]dioxin-2-yl)methyl)dimethylammonio)propane-1-sulfonate.

In one or more embodiments, the method of forming a polymer film or coating on a substrate from an aqueous solution of one or more hydrophilic EDOT-derived monomer(s) of the present invention includes any one or more of the above referenced embodiments of the first aspect of the present invention wherein the hydrophilic EDOT monomer has the formula:

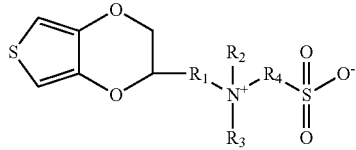

(I)

where $R_1$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_m$— or —(CH$_2$)$_y$O(CH$_2$)$_x$—; $R_2$ is —H, —CH$_3$, —CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; $R_3$ is —H, —CH$_3$, —CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; and $R_4$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_x$—, or —(CH$_2$)$_v$O(CH$_2$)$_w$—; and m, x, y, v and w are each an integer from 1 to 20

In one or more embodiments, the method of forming a polymer film or coating on a substrate from an aqueous solution of one or more hydrophilic EDOT-derived monomer(s) of the present invention includes any one or more of the above referenced embodiments of the first aspect of the present invention wherein the hydrophilic EDOT monomer has a formula selected from:

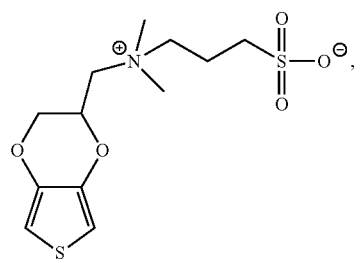

(II)

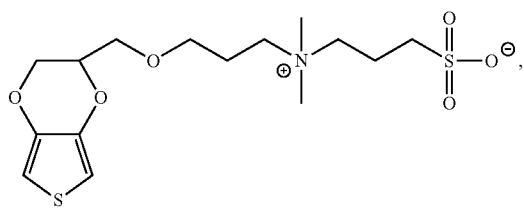

(III)

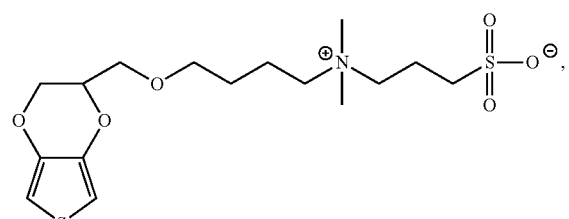

(IV)

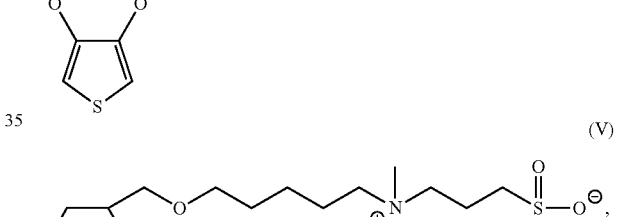

(V)

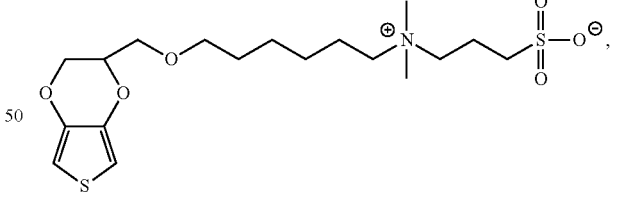

(VI)

and/or combinations thereof.

In one or more embodiments, the method of forming a polymer film or coating on a substrate from an aqueous solution of one or more hydrophilic EDOT-derived monomer(s) of the present invention includes any one or more of the above referenced embodiments of the first aspect of the present invention wherein the hydrophilic EDOT monomer is zwitterionic. In one or more embodiments, the method of forming a polymer film or coating on a substrate from an aqueous solution of one or more hydrophilic EDOT-derived monomer(s) of the present invention includes any one or more of the above referenced embodiments of the first aspect of the present invention wherein the concentration of hydrophilic EDOT monomer in the solution is from about 0.001 mM to about 1000 mM. In one or more embodiments, the method of forming a polymer film or coating on a substrate from an aqueous solution of one or more hydrophilic EDOT-derived monomer(s) of the present invention includes any one or more of the above referenced embodiments of the first aspect of the present invention wherein the the solution further comprises an electrolyte selected from the group consisting of $LiClO_4$, NaCl, KCl, $Na_2HPO_4$, $NaH_2PO_4$, $CaCl_2$, $MgCl_2$, $CaSO_4$, $MgSO_4$, and combinations thereof.

In one or more embodiments, the method of forming a polymer film or coating on a substrate from an aqueous solution of one or more hydrophilic EDOT-derived monomer(s) of the present invention includes any one or more of the above referenced embodiments of the first aspect of the present invention wherein the concentration of the electrolyte in the solution is from about 0.1 mM to about 1000 mM. In one or more embodiments, the method of forming a polymer film or coating on a substrate from an aqueous solution of one or more hydrophilic EDOT-derived monomer(s) of the present invention includes any one or more of the above referenced embodiments of the first aspect of the present invention wherein the step of applying an electric current further comprises applying a cyclic voltage of from −0.6 V to 1.3 V. In one or more embodiments, the method of forming a polymer film or coating on a substrate from an aqueous solution of one or more hydrophilic EDOT-derived monomer(s) of the present invention includes any one or more of the above referenced embodiments of the first aspect of the present invention wherein the step of applying an electric current comprises applying a current density of 0.01 $mA/cm^2$ to 100 $mA/cm^2$.

In a second aspect, the present invention is directed to a PSBEDOT polymer coating made using the method described above in the first aspect of the invention. In some embodiments, the PSBEDOT polymer coating has a cationic (oxidized) state and a zwitterionic (reduced) state. In one or more embodiments, the PSBEDOT polymer coating of the present invention includes any one or more of the above referenced embodiments of the second aspect of the present invention having an interfacial impedance that is less than 60% of the surface to which it is applied. In one or more embodiments, the PSBEDOT polymer coating of the present invention includes any one or more of the above referenced embodiments of the second aspect of the present invention having a protein adsorption of from 200 $ng/cm^2$ to 0.001 $ng/cm^2$ in human blood plasma in its reduced state. In one or more embodiments, the PSBEDOT polymer coating of the present invention includes any one or more of the above referenced embodiments of the second aspect of the present invention having a protein adsorption of from 200 $ng/cm^2$ to 0.001 $ng/cm^2$ in 30% human blood serum in its reduced state.

BRIEF DESCRIPTION OF THE DRAWINGS

For a more complete understanding of the features and advantages of the present invention, reference is now made to the detailed description of the invention along with the accompanying figures in which:

FIG. 2A is a comparison of the cyclic voltammograms of PSBEDOT after 1 and 500 cycles of applied potential; and FIG. 2B is a graph showing electrochemical impedance spectra (Bode plots) of bare gold substrate and PSBEDOT coated gold substrate.

FIG. 4A shows the PSBEDOT coated region; FIG. 4B shows the region across coating boundary; and FIG. 4C shows an uncoated region.

FIGS. 5A-D are images showing the results of cell adhesion tests. FIGS. 5A and 5B show the results of cell adhesion tests performed on PSBEDOT coated surfaces according to one or more embodiments of the present invention with BAEC (FIG. 5A) NIH 3T3 (FIG. 5B) fibroblasts; and FIGS. 5C and 5D show the results of cell adhesion tests performed on PEDOT coated gold substrate with BAEC (FIG. 5C) and NIH 3T3 (FIG. 5D) fibroblasts for 24 hours.

FIGS. 11A-B are XPS profiles of a PSBEDOT coating prepared according to one or more embodiments of the present invention. FIG. 11A is a survey spectrum and FIG. 11B is a high-resolution spectrum of S 2p peaks on FIG. 11A.

FIG. 12A shows the PSBEDOT coated surface; FIG. 12B shows the PEDOT coated surface, FIG. 12C shows the bare gold sensor chip surface.

DETAILED DESCRIPTION OF THE ILLUSTRATIVE EMBODIMENTS

Figure 1A:
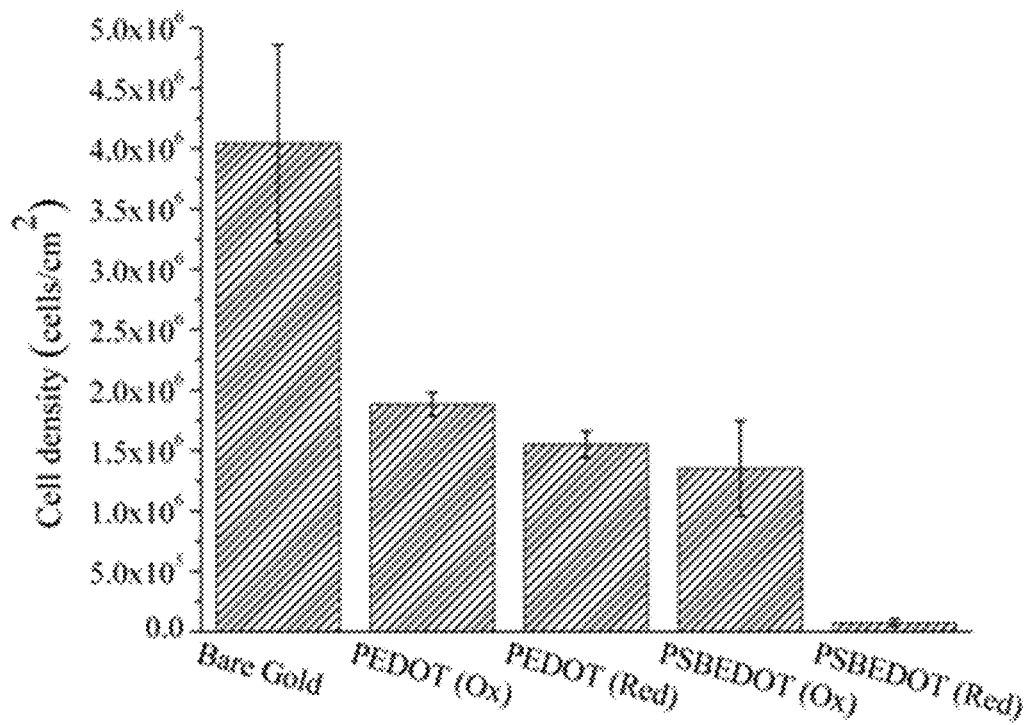
FIG. 1A is a graph showing quantitative data on the attachment of E. coli K12 from a suspension with $10^9$ cells/mL on oxidized PSBEDOT, reduced PSBEDOT and control surfaces.

In one or more embodiments, the present invention provide a method of forming compact, flexible, stable and biocompatible conducting polymer coatings for bioelectronics devices that uses a monomer is that is highly water-soluble and can be directly polymerized in aqueous solution without using organic solvents or surfactants, which are incompatible with most bioelectronics applications. In various embodiments, these polymer coatings maintain electro-switchable antimicrobial/antifouling properties and have excellent electrical conducting properties to minimize infection, increased biocompatibility, and improved bioelectronics performance. In one or more embodiments, the present invention relates to a novel method of synthesizing a sulfobetaine-functionalized conjugated polymer platform using 3,4-ethylenedioxythiophene (EDOT) as the conducting backbone (SBEDOT). This SBEDOT monomer is highly water-soluble and can be directly polymerized to form a densely packed film/coating on conductive or semi-conductive surfaces through electro-polymerization in a 100% aqueous solution without the need for organic solvents or surfactants. These polySBEDOT (PSBEDOT) coated surfaces have been shown to have electro-switchable antimicrobial/antifouling properties and excellent electrically conducting properties, which minimize infection, increase biocompatibility, and improve the performance of bioelectronics.

As set forth above, much effort has been devoted to develop flexible, stable and biocompatible conducting polymer based bioelectronics devices, but the starting materials are either poorly water-soluble or need the addition of surfactants to improve the aqueous processability. While other methods of forming polymers from hydrophilic and polar EDOT based monomers are known, it is believed that successful electro-polymerization of hydrophilic EDOT based monomers in an aqueous medium has not previously been accomplished. The ability of the SBEDOT monomers used in various embodiments of the method if the present invention to be directly polymerized in aqueous solution without the need for organic solvents or surfactants is one of the more significant advantages of the present method and will significantly facilitate its future various in vivo applications. Further, it should be appreciated that electro-polymerization methods provide a very attractive approach to the preparation of conjugated polymer surfaces since they offer a precise control of polymer film growth on the electrode surfaces by simply adjusting the concentration of the monomer and the potential/current and/or reaction time.

In a first aspect, the present invention is directed to a method of forming compact, flexible, stable and biocompatible conducting polymer films or coatings in an aqueous solution of hydrophilic EDOT-derived monomer(s). In general outline, the method involves the steps of: selecting a suitable substrate having a conductive or semiconductive surface; preparing a hydrophilic EDOT monomer comprising a terminal EDOT group and a betaine group, preferably a sulfobetaine group; dissolving the hydrophilic EDOT monomer in water or an aqueous solution, optionally adding an electrolytic compound; placing the substrate in the solution so that the solution is in contact with the surface of said substrate; and applying an electric current to the solution using standard electropolymerization techniques, causing the hydrophilic EDOT monomer to polymerize on the surface of the substrate.

The substrate is not particularly limited provided that the surface onto which the hydrophilic EDOT monomer will polymerize is conductive or, at least semi-conductive. Suitable substrates may include, without limitation, implantable medical devices, steel/stainless steel, titanium/titanium alloy, silicon, ITO coated substrates, gold coated substrates, aluminum/aluminum alloy, platinum, noble metals, or any combination thereof. Likewise, any conductive or semi-conductive surface capable of conducting sufficient current to permit polymerization of the conductive or, at least semi-conductive thereon may be used including, but not limited to, surfaces comprising steel/stainless steel, titanium/titanium alloy, aluminum/aluminum, alloys, silicon, iridium tin oxide (ITO), gold, platinum, noble metals, or alloys and combination thereof.

As set forth above, the hydrophilic EDOT based monomer used in the method of the present invention comprises a terminal EDOT group and a betaine group, which is preferably a sulfobetaine group, and should be readily soluble in water and aqueous solutions without the need for co-solvents or surfactants. Suitable hydrophilic EDOT monomers may include, without limitation, 3-(((2,3-dihydrothieno[3,4-b][1,4]dioxin-2-yl)methyl)dimethylammonio)propane-1-sulfonate, 3-((3-((2,3-dihydrothieno[3,4-b][1,4]dioxin-2-yl)methoxy)propyl)dimethylammonio) propane-1-sulfonate, 3-((4-((2,3-dihydrothieno[3,4-b][1,4]dioxin-2-yl)methoxy)butyl)dimethylammonio)propane-1-sulfonate, 3-((5-((2,3-dihydrothieno[3,4-b][1,4]dioxin-2-yl)methoxy)pentyl)dimethylammonio)propane-1-sulfonate, 3-((6-((2,3-dihydrothieno[3,4-b][1,4]dioxin-2-yl)methoxy)hexyl) dimethylammonio) propane-1-sulfonate, or any combination thereof. In one or more embodiment, hydrophilic EDOT monomer is zwitterionic.

In one or more embodiments, the hydrophilic EDOT monomer has the formula:

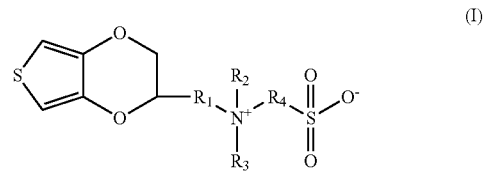

(I)

wherein $R_1$ is —$CH_2$—, —$CH_2CH_2$—, —$CH_2CH_2CH_2$—, —$CH_2CH_2CH_2CH_2$—, —$CH_2CH_2CH_2CH_2CH_2$—, —$(CH_2)_m$— or —$(CH_2)_yO(CH_2)_x$—; $R_2$ is —H, —$CH_3$, —$CH_2CH_3$, —$CH_2CH_2CH_3$, —$CH_2CH_2CH_2CH_3$, —$CH_2CH_2OH$, —$CH_2CH_2CH_2OH$, —$CH_2CH_2CH_2CH_2OH$, or —$CH_2CH_2CH_2CH_2CH_2OH$; $R_3$ is —H, —$CH_3$, —$CH_2CH_3$, —$CH_2CH_2CH_3$, —$CH_2CH_2CH_2CH_3$, —$CH_2CH_2OH$, —$CH_2CH_2CH_2OH$, —$CH_2CH_2CH_2CH_2OH$, or —$CH_2CH_2CH_2CH_2CH_2OH$; and $R_4$ is —$CH_2$—, —$CH_2CH_2$—, —$CH_2CH_2CH_2$—, —$CH_2CH_2CH_2CH_2$—, —$CH_2CH_2CH_2CH_2CH_2$—, —$(CH_2)_x$—, or —$(CH_2)_yO(CH_2)_w$—; and m, x, y, v and w are each an integer from 1 to 20

In some embodiments, the hydrophilic EDOT monomer has a formula selected from:

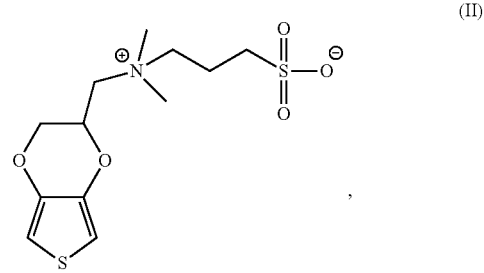

(II)

-continued

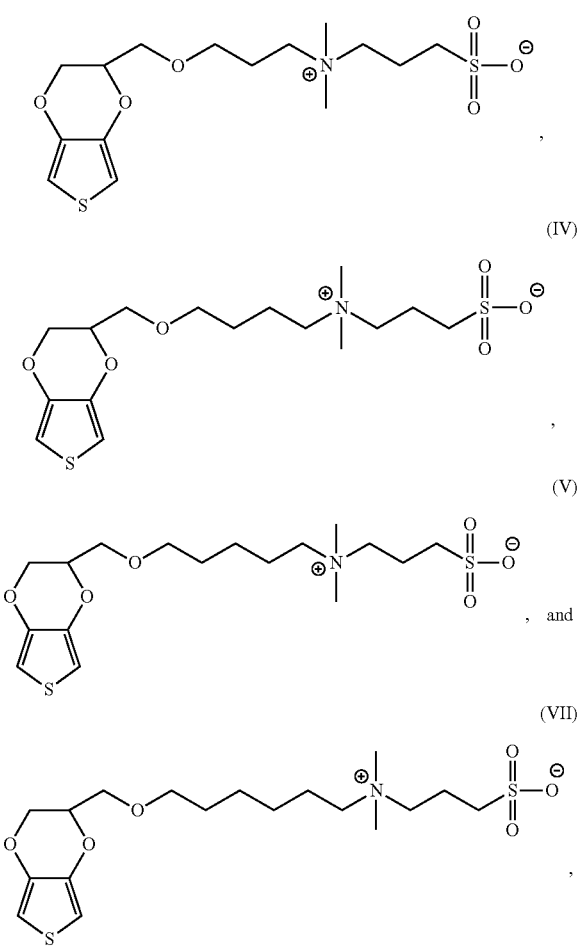

As set forth above, the hydrophilic EDOT monomer is dissolved in water or an aqueous solution, without the use of co-solvents, surfactants, or other solubilizing agents. In one or more embodiments, the concentration of hydrophilic EDOT monomer in the hydrophilic EDOT monomer solution may be from about 0.001 mM to about 1000 mM. In some embodiments, the concentration of hydrophilic EDOT monomer in the hydrophilic EDOT monomer solution may be 10 mM or more, in other embodiments 50 mM or more, in other embodiments 100 mM or more, in other embodiments 200 mM or more, in other embodiments 300 mM or more, in other embodiments 400 mM or more, and in other embodiments 500 mM or more. In some embodiments, the concentration of hydrophilic EDOT monomer in the hydrophilic EDOT monomer solution may be 900 mM or less, in other embodiments 850 mM or less, in other embodiments 800 mM or less, in other embodiments 750 mM or less, in other embodiments 700 mM or less, in other embodiments 600 mM or less, and in other embodiments 500 mM or less. In one or more embodiments, the concentration of hydrophilic EDOT monomer in the hydrophilic EDOT monomer solution may be from about 50 mM to about 100 mM. In one or more embodiments, the concentration of hydrophilic EDOT monomer in the hydrophilic EDOT monomer solution may be about 60 mM.

In one or more embodiments, the hydrophilic EDOT monomer solution may further comprise an electrolyte/or combination of eletrolytes to facilitate electro-polymerization. Suitable electrolytes may include, without limitation, $LiClO_4$, NaCl, KCl, $Na_2HPO_4$, $NaH_2PO_4$, $CaCl_2$, $MgCl_2$, $CaSO_4$, $MgSO_4$, and combinations thereof. In one or more embodiments, the concentration of electrolyte in the hydrophilic EDOT monomer solution may be from about 0.01 mM to about 1000 mM. In one or more embodiments, the concentration of electrolyte in the hydrophilic EDOT monomer solution may be 1 mM or more, in other embodiments, 10 mM or more, in other embodiments, 100 mM or more, in other embodiments, 200 mM or more, in other embodiments, 300 mM or more, in other embodiments, 400 mM or more, and in other embodiments, 500 mM or more. In one or more embodiments, the concentration of electrolyte in the hydrophilic EDOT monomer solution may be 900 mM or less, in other embodiments, 800 mM or less, in other embodiments, 700 mM or less, in other embodiments, 600 mM or less, in other embodiments, 500 mM or less, in other embodiments, 400 mM or less, and in other embodiments, 300 mM or less. In one or more embodiment, the concentration of electrolyte in the hydrophilic EDOT monomer solution may be about 100 mM.

Last, the hydrophilic EDOT monomers in the hydrophilic EDOT monomer solution are polymerized onto the conducting or semiconducting surface of the substrate using conventional electro-polymerization techniques. In one or more embodiments, cyclic voltammetry, galvanostatic, or potentiostatic electro-polymerization techniques may be used to form the compact, flexible, stable and biocompatible conducting polymer films or coatings. In one or more embodiment, electro-polymerization may be performed using cyclic voltammetry from −0.6 V to 1.3 V. In some other embodiments, electro-polymerization may be performed using galvanostatic method at 0.01-100 mA/cm². In some other embodiments, electro-polymerization may be performed using potentiostatic method at 0.5-1.3 V.

In one or more embodiment, the current applied for polymerization has a current density of from 0.01 mA/cm² to 100 mA/cm². In some embodiments, the current density applied for polymerization may be 0.1 mA/cm² or more, in other embodiments, 1.0 mA/cm² or more, in other embodiments, 5.0 mA/cm² or more, in other embodiments, 10.0 mA/cm² or more, in other embodiments, 15.0 mA/cm² or more, in other embodiments, 25 mA/cm² or more, and in other embodiments, 35 mA/cm² or more In some embodiments, the current density applied for polymerization may be 95 mA/cm² or less, in other embodiments, 90 mA/cm² or less, in other embodiments, 85 mA/cm² or less, in other embodiments, 80 mA/cm² or less, in other embodiments, 75 mA/cm² or less, in other embodiments, 70 mA/cm² or less, and in other embodiments, 60 mA/cm² or less.

In a second aspect, the present invention is directed to a PSBEDOT film or coating for use with biomaterials formed from a betaine containing, (more preferably a sulfobetaine containing) hydrophilic EDOT monomer using the novel method described above. These coatings have been found to have excellent conducting properties, superior antifouling properties, switchable antimicrobial properties, biocompatibility, and low interfacial impedance. As will be appreciated by those of skill in the art, a major challenge of implantable devices/biomaterials is the risk of surgical infection and in order to prevent these infections, antifouling and antimicrobial strategies are commonly used. PSBEDOT coatings according to various embodiments of the present invention have both a cationic antimicrobial state and zwitterionic antifouling state. Due to the unique structure of these zwitterionic conjugated PSBEDOT coatings, it is possible to switch between the antifouling and antimicrobial states by adjusting the potential of the surfaces. In the oxidized state, the PSBEDOT backbone is positively charged and the overall polymer becomes cationic, although the side chains are still neutral. In this state, the PSBEDOT coatings will have strong antimicrobial properties. Conversely, under the reduced state, PSBEDOT backbone is neutral, so overall polymer has no net charge. In this reduced state, the PSBEDOT coatings will have strong antifouling properties. By changing the potential applied to the coating, it is possible to switch back and forth between these oxidized and reduced states.

As set forth above, the PSBEDOT coatings according to one or more embodiments of the present invention exhibit excellent antimicrobial properties. These PSBEDOT coatings were found to kill over 89% of attached bacterial cells in one hour at 0.6 V in the oxidized antimicrobial state and then release over 96.7% of the dead cells in one hour at 0 V under static conditions in the reduced antifouling state. In some embodiments, these PSBEDOT coatings were found to kill over 90%, in other embodiments, over 92%, and in other embodiments, over 94% of attached bacterial cells in one hour at 0.6 V in the oxidized antimicrobial state. Similarly, In some embodiments, these PSBEDOT coatings were found to release over 97%, on other embodiments, over 97.5%, and in other embodiments, over 98% of adhered dead cells in one hour at 0 V under static conditions in the reduced antifouling state. These results were unexpectedly positive compared to similar prior art coatings. PSBEDOT coatings according to one or more embodiments of the present invention and show great promise for applications in bioelectronics.

Aside from its contribution to surgical infection, the adsorption of the protein by implanted bioelectronic devices is a leading cause of biofouling which can eventually lead to the failure of the bioelectronics device. As will be discussed in more detail below, PSBEDOT coatings according to one or more embodiments of the present invention have been found to have superior antifouling properties against single protein, whole blood, mammalian cells and bacteria.

In one or more embodiment, the PSBEDOT polymer coating the present invention has a protein adsorption of from 200 $ng/cm^2$ to 0.001 $ng/cm^2$ in human blood plasma in its reduced state. In some other embodiments, the PSBEDOT polymer coating the present invention has a protein adsorption of from 100 $ng/cm^2$ to 0.001 $ng/cm^2$ in human blood plasma in its reduced state. In some other embodiments, the PSBEDOT polymer coating the present invention has a protein adsorption of from 50 $ng/cm^2$ to 0.001 $ng/cm^2$ in human blood plasma in its reduced state. In some other embodiments, the PSBEDOT polymer coating the present invention has a protein adsorption of from 200 $ng/cm^2$ to 0.01 $ng/cm^2$ in human blood plasma in its reduced state. In some other embodiments, the PSBEDOT polymer coating the present invention has a protein adsorption of from 200 $ng/cm^2$ to 0.1 $ng/cm^2$ in human blood plasma in its reduced state. In some other embodiments, the PSBEDOT polymer coating the present invention has a protein adsorption of from 200 $ng/cm^2$ to 1 $ng/cm^2$ in human blood plasma in its reduced state.

In one or more embodiment, the PSBEDOT polymer coating the present invention has a protein adsorption of from 200 $ng/cm^2$ to 0.001 $ng/cm^2$ in 30% human blood serum in its reduced state. In some other embodiments, the PSBEDOT polymer coating the present invention has a protein adsorption of from 100 $ng/cm^2$ to 0.001 $ng/cm^2$ in 30% human blood serum in its reduced state. In some other embodiments, the PSBEDOT polymer coating the present invention has a protein adsorption of from 10 $ng/cm^2$ to 0.001 $ng/cm^2$ in 30% human blood serum in its reduced state. In some other embodiments, the PSBEDOT polymer coating the present invention has a protein adsorption of from 200 $ng/cm^2$ to 0.01 $ng/cm^2$ in 30% human blood serum in its reduced state. In some other embodiments, the PSBEDOT polymer coating the present invention has a protein adsorption of from 200 $ng/cm^2$ to 0.1 $ng/cm^2$ in 30% human blood serum in its reduced state. In some other embodiments, the PSBEDOT polymer coating the present invention has a protein adsorption of from 200 $ng/cm^2$ to 1 $ng/cm^2$ in 30% human blood serum in its reduced state. In some other embodiments, the PSBEDOT polymer coating the present invention has a protein adsorption of from 200 $ng/cm^2$ to 10 $ng/cm^2$ in 30% human blood serum in its reduced state.

In addition, PSBEDOT coatings according to one or more embodiments of the present invention have excellent electrical properties. Unlike traditional biomaterials, these coatings allow for the smaller electrical stimulation of the attached tissues and cells or higher sensitivity for the detection of the electrical signals It will be appreciated that to deliver or detect lower electrical signals, both high electrical stability and low interfacial impedance are highly desired for bioelectronics. PSBEDOT coatings according to one or more embodiments of the present invention have been found to significantly decrease the interfacial impedance of gold electrodes, for example, which significantly improves signal collection and charge delivery of the bioelectronics.

In one or more embodiments, PSBEDOT coatings of the present invention may have an interfacial impedance that is less than 60% of the surface to which it is applied. In some other embodiments, the interfacial impedance may be less than 50% of the surface to which it is applied. In some other embodiments, the interfacial impedance may be less than 40% of the surface to which it is applied. In some other embodiments, the interfacial impedance may be less than 30% of the surface to which it is applied. In some other embodiments, the interfacial impedance may be less than 20% of the surface to which it is applied. In some other embodiments, the interfacial impedance may be less than 10% of the surface to which it is applied.

In one or more embodiments, the interfacial impedance of PSBEDOT is less than 10% of that of bare gold at low frequency, which leads to higher sensitivity for the sensor. In one or more embodiments, the interfacial impedance of PSBEDOT is less than 10% of that of bare gold at frequency of less than 1000 Hz. In one or more embodiments, the interfacial impedance of PSBEDOT is less than 9% of bare gold at frequency of about less than 1000 Hz. In one or more embodiments, the interfacial impedance of PSBEDOT is less than 8% of that of bare gold at frequency of about less than 1000 Hz. In one or more embodiments, the interfacial impedance of PSBEDOT is less than 6% of bare gold at frequency of about less than 1000 Hz.

Overall, it is believed that PSBEDOT coatings according to one or more embodiment of the present invention will significantly increase the performance and service life, minimize foreign body reaction, improve biocompatiblity and reduce the infection of the bioelectronic devices.

EXPERIMENTAL

PSBEDOT was synthesized using the mechanism shown in Scheme 1.

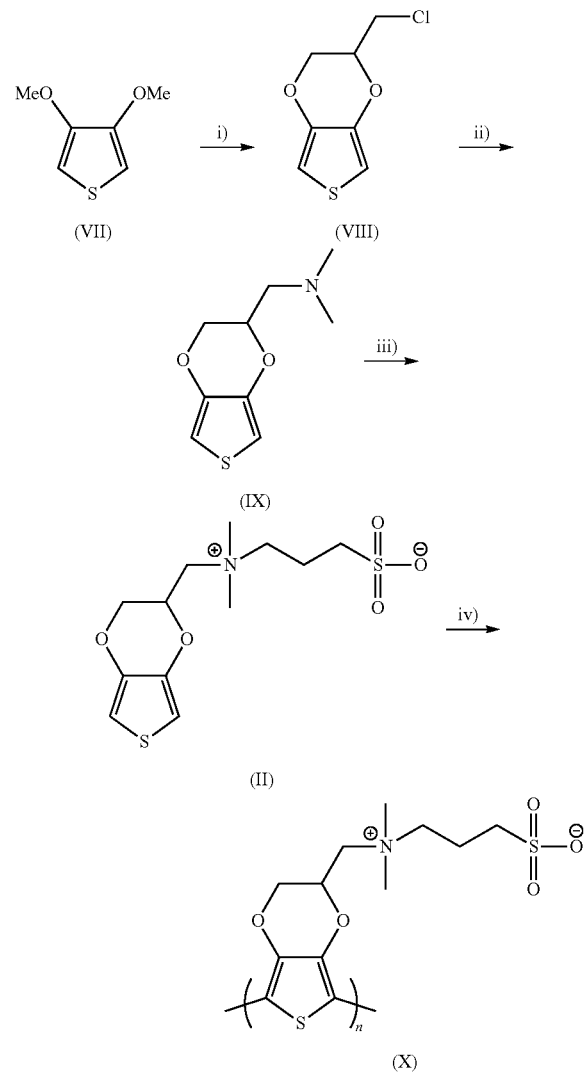

Scheme 1.
Synthetic route of PSBEDOT.

Reaction conditions: i) 3-chloropropane-1,2-diol, p-toluenesulfonic acid, toluene; ii) dimethylamine, water, acetonitrile; iii) 1,3-propanesultone, tetrahydrofuran; iv) electropolymerization in aqueous solution.

Figure 6:
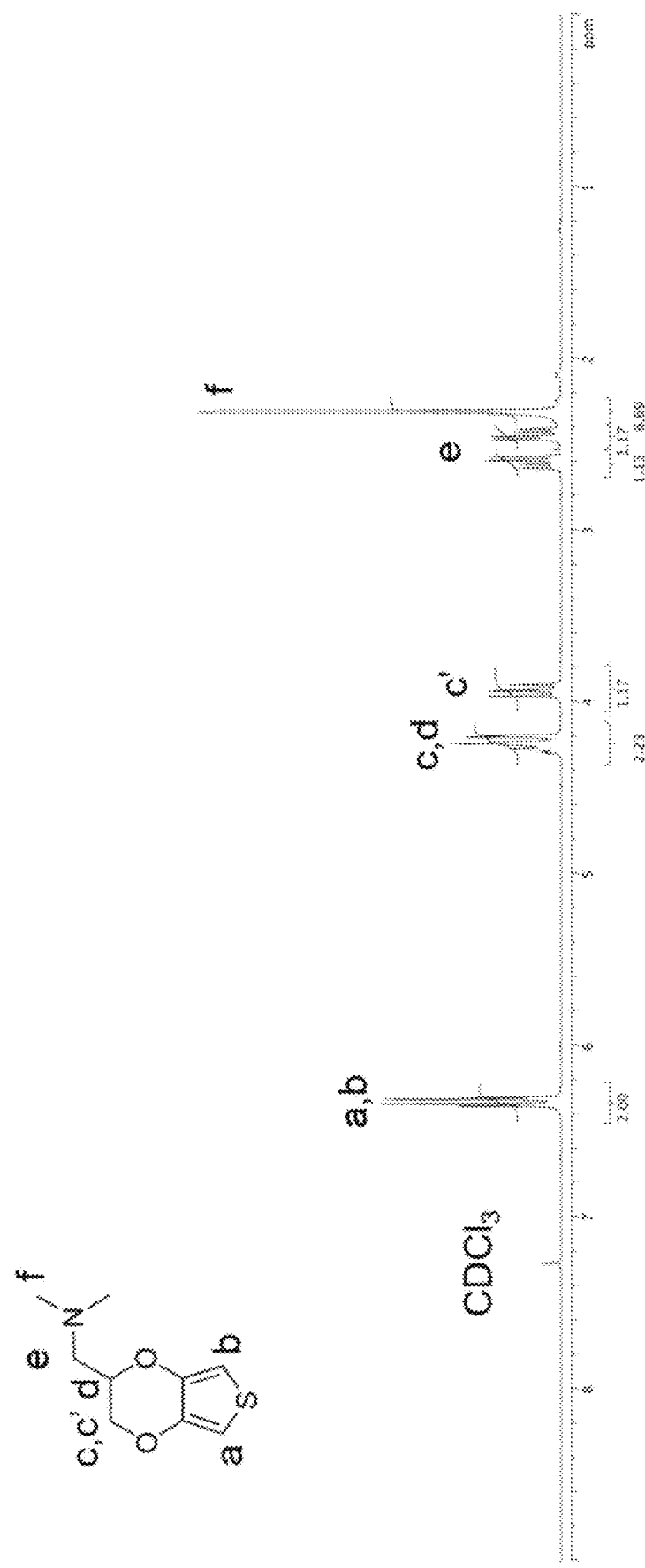
FIG. 6 is a $^1H$ NMR spectrum of EDOT-DMA
Figure 7:
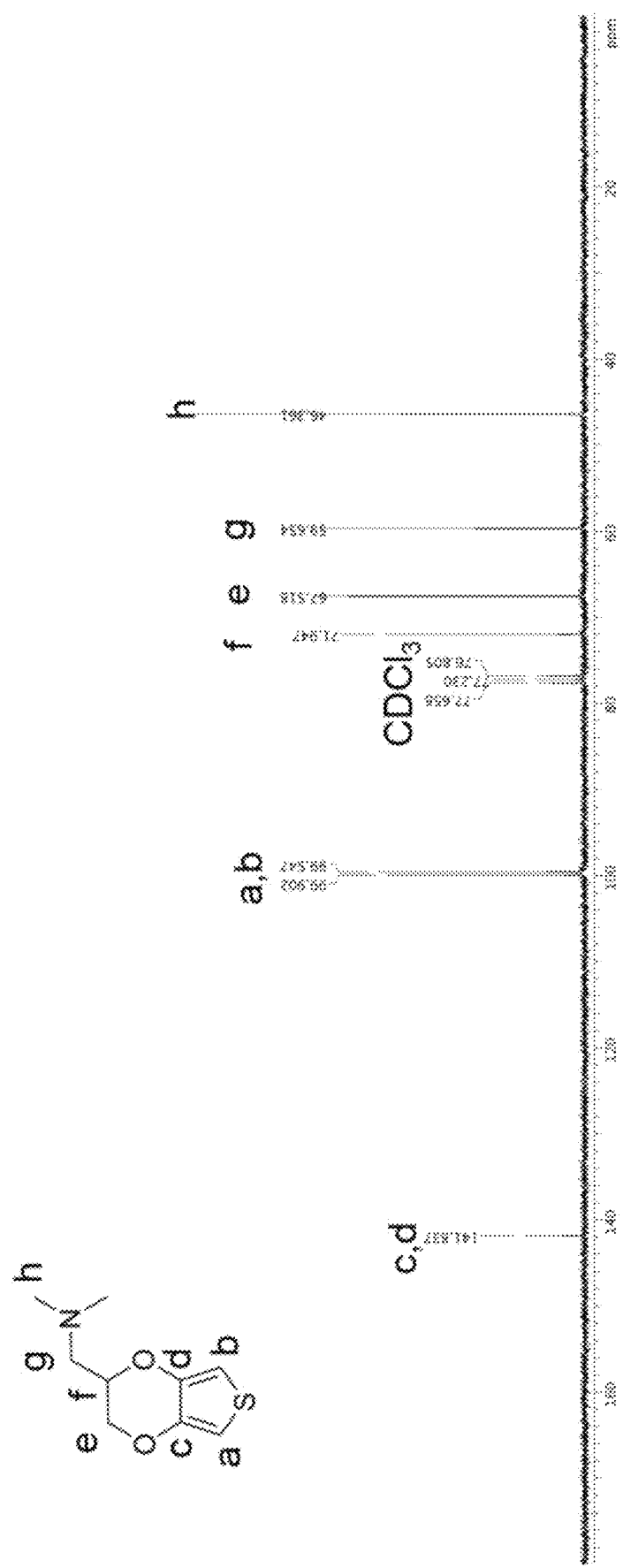
FIG. 7 is a $^{13}C$ NMR spectrum of EDOT-DMA
Figure 8:
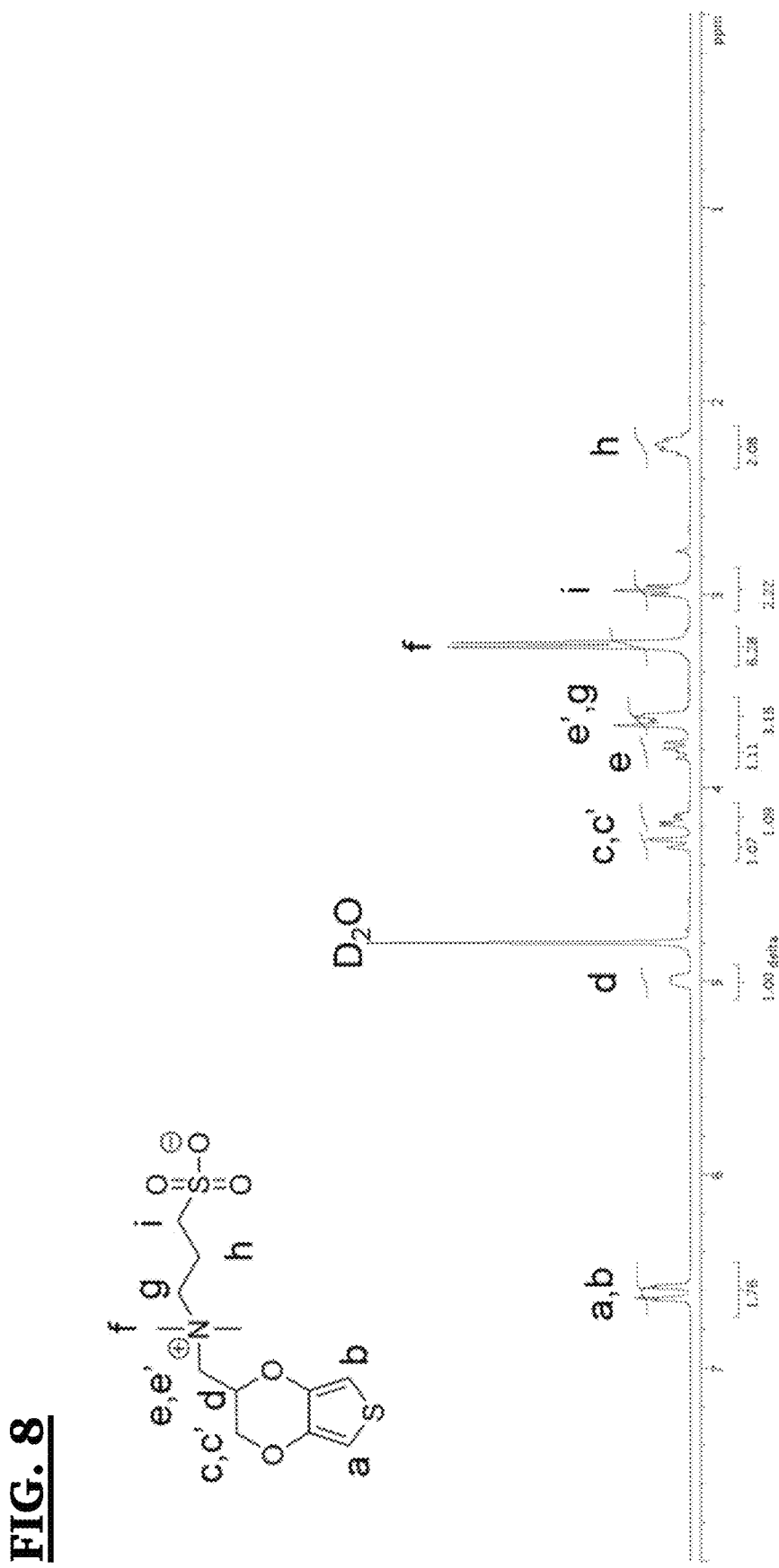
FIG. 8 is a $^1H$ NMR spectrum of SBEDOT prepared according to one or more embodiments of the present invention.
Figure 9:
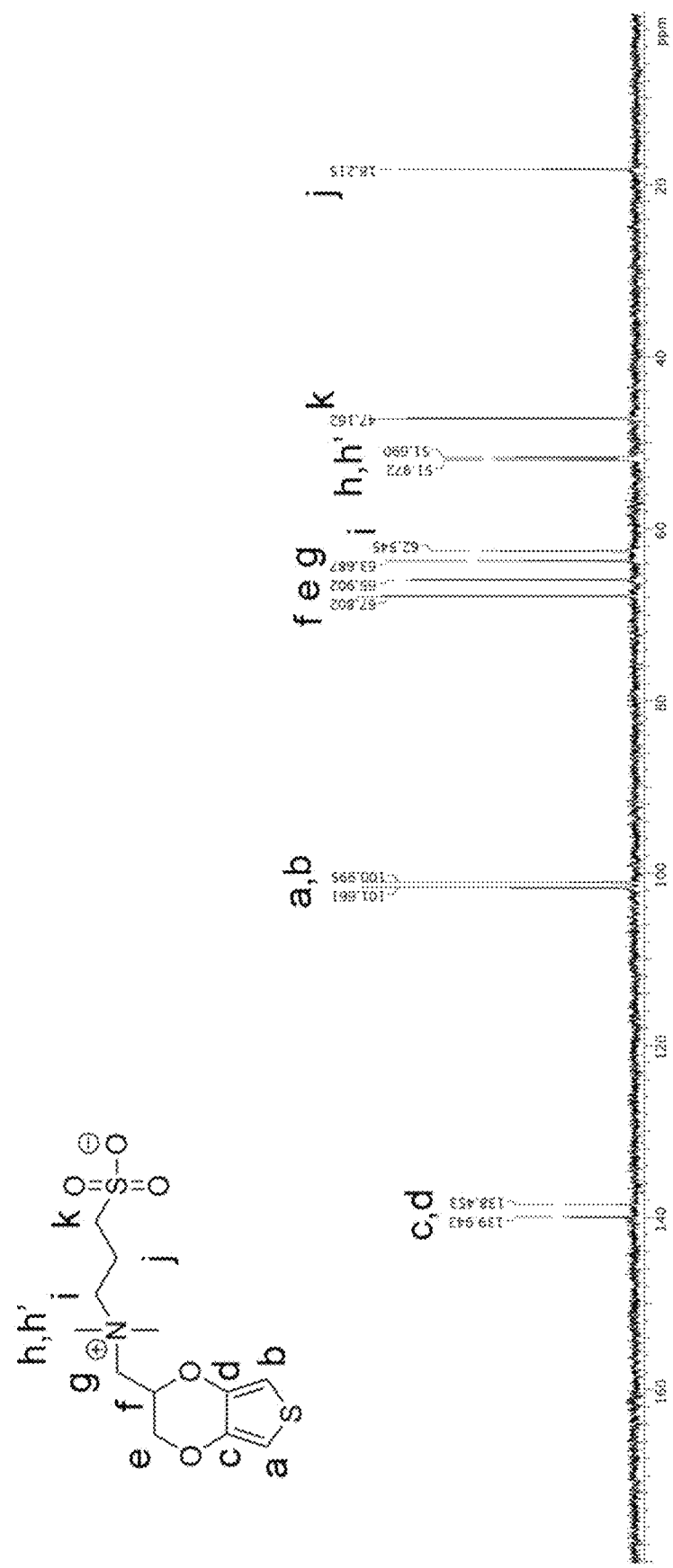
FIG. 9 is a $^{13}C$ NMR spectrum of SBEDOT prepared according to one or more embodiments of the present invention.

As can be seen in Scheme 1 above, EDOT-Cl (VIII) was synthesized from 3,4-dimethoxythiophene (VII) using 3-chloropropane-1,2-diol, p-toluenesulfonic acid, and toluene. (See the procedures set forth in T. Erb, U. Zhokhavets, G. Gobsch, S. Raleva, B. Stuhn, P. Schilinsky, C. Waldauf and C. J. Brabec, "Correlation Between Structural and Optical Properties of Composite Polymer/Fullerene Films for Organic Solar Cells," *Adv Funct Mater*, 2005, 15, 1193-1196, the disclosure of which is incorporated herein by reference in its entirety.) Next, a straightforward amination of EDOT-Cl using 3-chloropropane-1,2-diol, p-toluenesulfonic acid and toluene to produce EDOT-dimethylamine (EDOT-DMA) (IX) (see FIGS. 6-7), followed by the quaternization with 1,3-propanesultone using 1,3-propanesultone and tetrahydrofuran, produced the target zwitterionic compound SBEDOT monomer (II) with a good overall yield. The pure monomer product was fully characterized with $^1H$ and $^{13}C$ nuclear magnetic resonance (NMR) spectroscopy. See, FIGS. 8-9. The SBEDOT monomer (II) is then electro-polymerized to form the corresponding PSBEDOT polymer (X).

Both cyclic voltammetry (CV) and galvanostatic (GS) methods were used to electro-polymerize SBEDOT on various substrates, from an aqueous solution containing 60 mM monomer and 100 mM $LiClO_4$ as electrolyte. Zwitterionic PSBEDOT was successfully coated on both indium tin oxide coated polyethylene terephthalate (ITO-PET) substrate and gold coated SPR sensor chips. The surfaces prepared from GS method showed much better homogeneity than those generated from CV. It was noticed that, during the GS electro-polymerization process, the working potential decreases smoothly with the increase of reaction time, indicating the decrease of overall impedance and reflecting the excellent electrical conductivity of the deposited PSBEDOT films. EDOT monomer was also polymerized using the similar method on same substrates and PEDOT surface was used as a control throughout these experiments. It is believed that the successful film deposition of PSBEDOT might be the result of the high polymerization rate, high molecular weight and anti-electrolyte effect of PSBEDOT polymers.

To confirm the successful surface deposition of materials, the detailed chemical composition of the PSBEDOT surface was analyzed with X-ray photoelectron spectroscopy (XPS). Peak areas, line shapes, and intensities of C 1s, O 1s, N 1s and S 2p high resolution spectra were monitored. In the survey spectrum of PSBEDOT (FIG. 1A), the presence of N and doublet of S, which were not present in PEDOT, indicated that PSBEDOT was successfully deposited onto the substrate. The atomic ratios were also in agreement with molecular compositions. The detailed high-resolution spectrum of S 2p (FIG. 1B) showed that two types of S were observed with nearly equivalent peak intensities, which confirmed the immobilized homopolymer PSBEDOT with equal amount of sulfur atoms on both the thiophene rings and ionic sulfonate side chains.

Figure 2A:
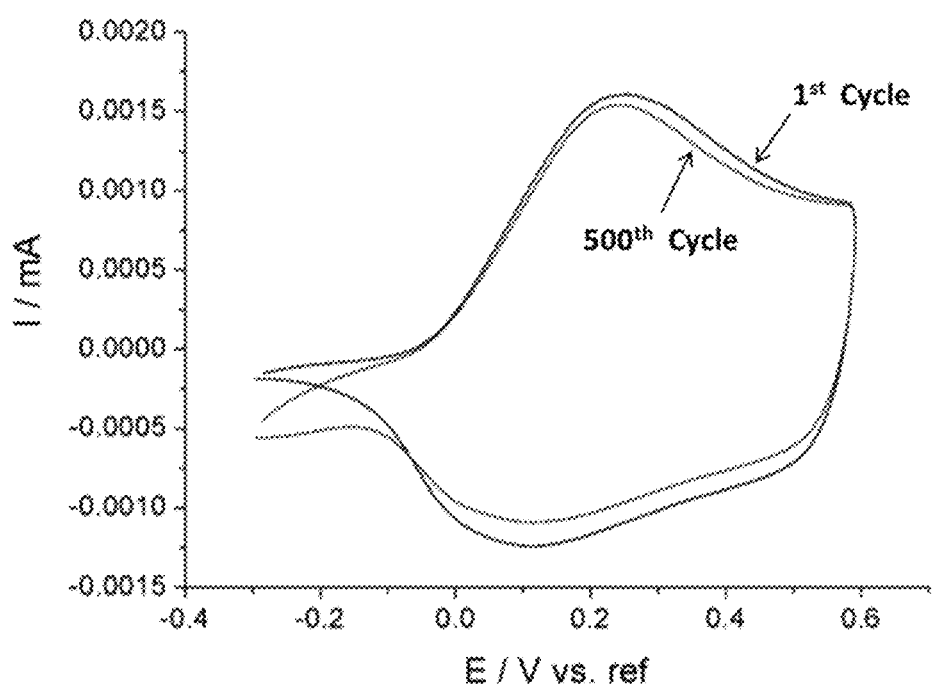
FIGS. 2A-B are electrochemical characterizations of PSBEDOT films prepared according to one or more embodiments of the present invention.
Figure 2B:
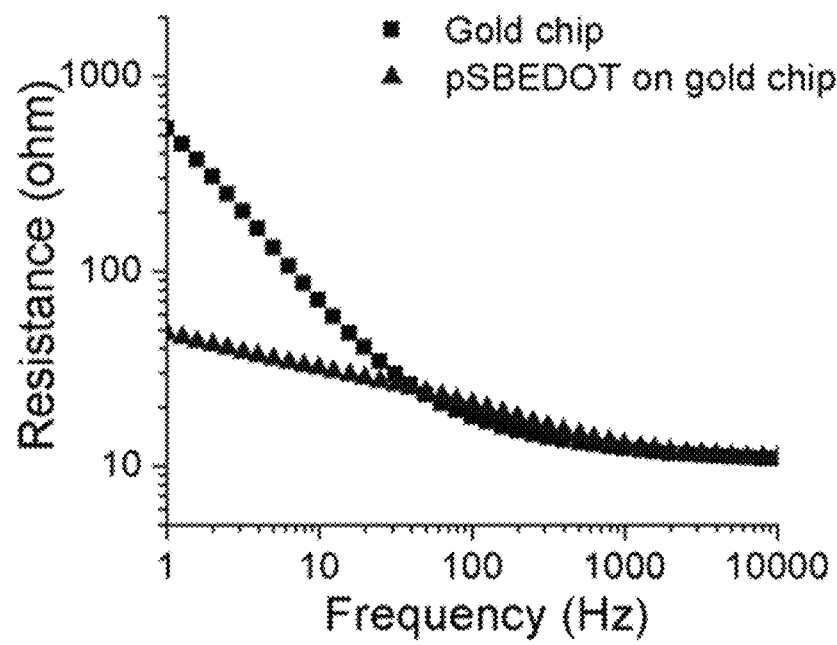

For delivering/detecting lower electrical signals, both high electrical stability and low interfacial impedance are highly desired for bioelectronics. Cyclic voltammetry (CV) and electrochemical impedance spectroscopy (EIS) were used to analyze the electrochemical properties of the coated films. The PSBEDOT films showed good stability, with slight decrease of electro-activity after CV sweeping for 500 cycles from −0.3 to 0.6 V vs $Hg/HgCl_2$ electrode (FIG. 2A). EIS was performed on both coated and uncoated substrates. The impedance of the coated substrates was about 10 times lower than the uncoated gold at low frequencies (FIG. 2B), which is comparable to that of PEDOT and suggests a densely packed polymer layer formed. The result indicates that the PSBEDOT can significantly decrease the interfacial impedance of the gold electrode, which significantly improve signal collection and charge delivery of the bioelectronics.

Figure 3:
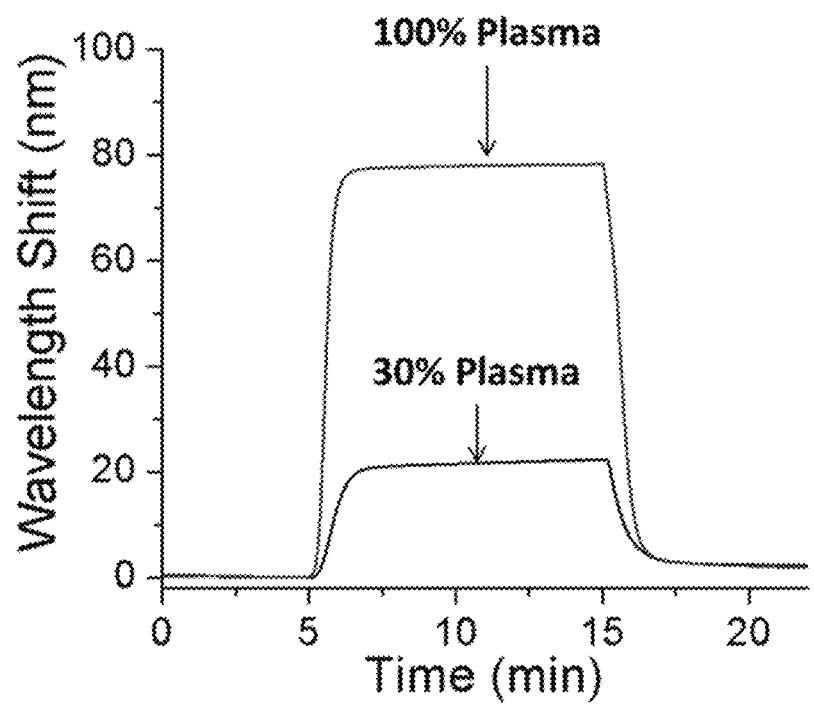
FIG. 3 is a representative SPR sensorgrams of PSBEDOT coated sensor chips according to one or more embodiments of the present invention showing the low protein adsorption from 100% human blood plasma and 30% human blood serum.

As set forth above, the adsorption of the protein is a leading cause of biofouling phenomena, which eventually lead to the failure of bioelectronics. A four-channel surface plasmon resonance (SPR) sensor was used to evaluate the antifouling property of PSBEDOT coated gold chips using 100% human blood plasma and 30% human blood serum. As shown in FIG. 3, the PSBEDOT coated gold surface prepared according to one or more embodiments of the present invention is highly resistant to the protein adsorption from both 100% human blood plasma and 30% human blood serum. The adsorption amount was about 28 ng/cm$^{-2}$ for plasma and 33 ng/cm$^{-2}$ for serum.

For coatings, the packing density and surface roughness are two important factors for their antifouling properties. Compared to the polymer brushes generated from Atom Transfer Radical Polymerization (ATRP), the polymer films obtained from electrochemical polymerization may not be as densely packed and well oriented, so it may increase the specific surface area of the substrate. Therefore, it is possible the polymer architecture and high surface area from electrochemical polymerization slightly compromise the antifouling performance; however, from the stand of applications, electro-polymerized surfaces are easy to prepare and more flexible in controlling film thickness compared to polymer brushes-based surfaces.

Figure 4A:
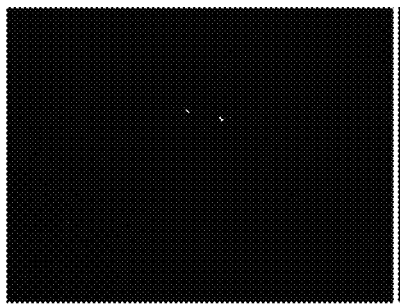
FIG. 4A-C are images showing the results of BAECs adhesion test with PSBEDOT coated ITO-PET prepared according to one or more embodiments of the present invention.
Figure 4B:
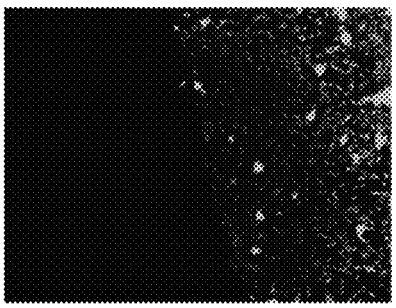
Figure 4C:
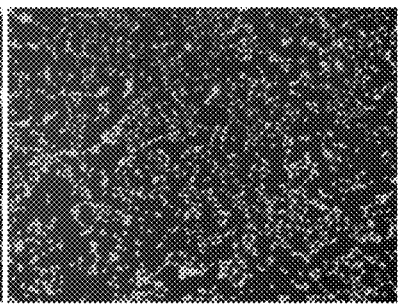
Figure 5A:
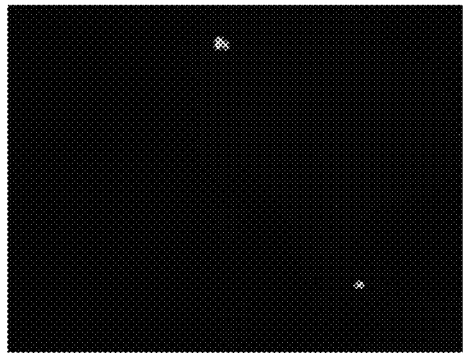
Figure 5B:
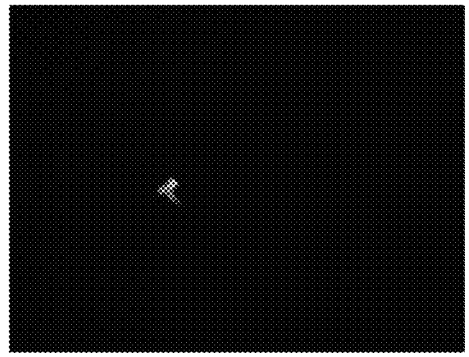
Figure 5A:
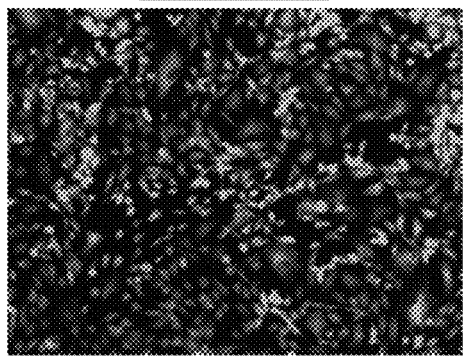
Figure 5A:
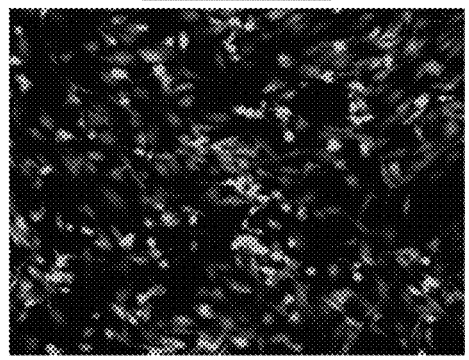

To further evaluate antifouling properties of PSBEDOT surfaces according to one or more embodiments of the present invention, cell attachment studies were performed using both bovine aorta endothelial cells (BAECs) and mice NIH 3T3 fibroblast cells. PSBEDOT and PEDOT surfaces were prepared from GS electro-polymerization of SBEDOT and EDOT monomers on both ITO-PET surface and gold-coated SPR sensor chips. (See Examples, below). All cells were incubated with the substrates at 37° C. for 24 hours before imaging. For PSBEDOT coated ITO-PET, a significant difference was seen on the coated and uncoated regions across the coating edge. Large amount of cells was found on the uncoated area of ITO-PET, while very few cells were found on the PSBEDOT coating site (FIGS. 4A-C). Both PSBEDOT and PEDOT were coated on gold SPR substrates to compare their antifouling behavior. Nearly full coverage of BAECs and NIH 3T3 fibroblast cells was seen on PEDOT surfaces, while there was almost no cell attached on the PSBEDOT surfaces (FIGS. 5A-D). The density of adhered BAECs and NIH 3T3 fibroblast cells on PSBEDOT surfaces was 0.7% and 0.9% of that on the PEDOT surfaces (See, Table 1). These results demonstrated that we have successfully developed an antifouling PSBEDOT coating that highly resists cell adhesion.

TABLE 1

Percentage of the attached cells on PSBEDOT surfaces relative to PEDOT coated surfaces (n = 3)

|  | BAECs on PSBEDOT | BAECs on PEDOT | NIH-3T3 on PSBEDOT | NIH-3T3 on PEDOT |
|---|---|---|---|---|
| % of cell attachment | 0.7 ± 0.2 | 100 ± 3.6 | 0.9 ± 0.4 | 100 ± 11.2 |

One major challenge of implantable devices/materials is the surgical infection. To prevent infection, antifouling and antimicrobial strategies are commonly used. As set forth above, due to the unique structure of zwitterionic conjugated PSBEDOT, it can switch between the antifouling and antimicrobial states by adjusting the potential of the surfaces. To evaluate PSBEDOT's potential to minimize infection, bacterial adhesion, antimicrobial and releasing studies on PSBEDOT surfaces were conducted by using E. coli K12 as a model cell. Before the attachment study, PSBEDOT substrates were equilibrated at 0.6 or 0 V in PBS for 30 minutes to generate oxidized and reduced PSBEDOT surface respectively. The bacterial attachment study (FIG. 1) showed that reduced PSBEDOT surfaces is highly resistant to E. coli K12. The cell density on reduced PSBEDOT surfaces is less than 1.9% of that on gold surfaces. The attachment of E. coli K12 on oxidized PSBEDOT surfaces increases to 33.4% relative to bare gold. The density of the attached E. coli K12 on both oxidized and reduced PEDOT surfaces were high (46.6% and 38.4% relative to gold).

Figure 1B:
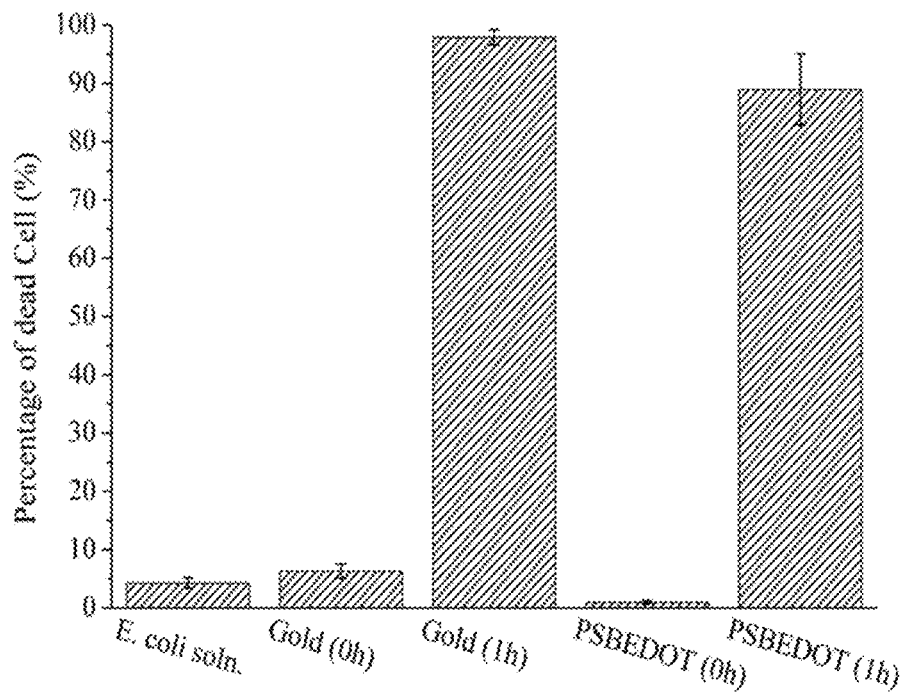
FIG. 1B is a graph showing quantitative data on bactericidal activity of PSBEDOT and control surface against E. coli K12 at 0.6 V for 1 hour.

To proof that the oxidized PSBEDOT can kill the attached bacterial cells. PSBEDOT substrates with attached cells described above were submerged in the PBS and 0.6 V potential was applied for 1 hour. The viability of the bacterial cells before and after applying the potential was analyzed by LIVE/DEAD® Cell Viability Assays using the fluorescence microscope. Results in FIG. 1B show that PSBEDOT surfaces kill >89% of the E. coli in one hour and gold substrates kill >97.9% of the attached cells. In solution, over 95.8% of E. coli K12 are viable. While the gold killed more of the bacterial cells than did the PSBEDOT surfaces, it should be noted that the gold does not have the ability to subsequently release the dead cells as does the PSBEDOT coating of the present invention.

Figure 1C:
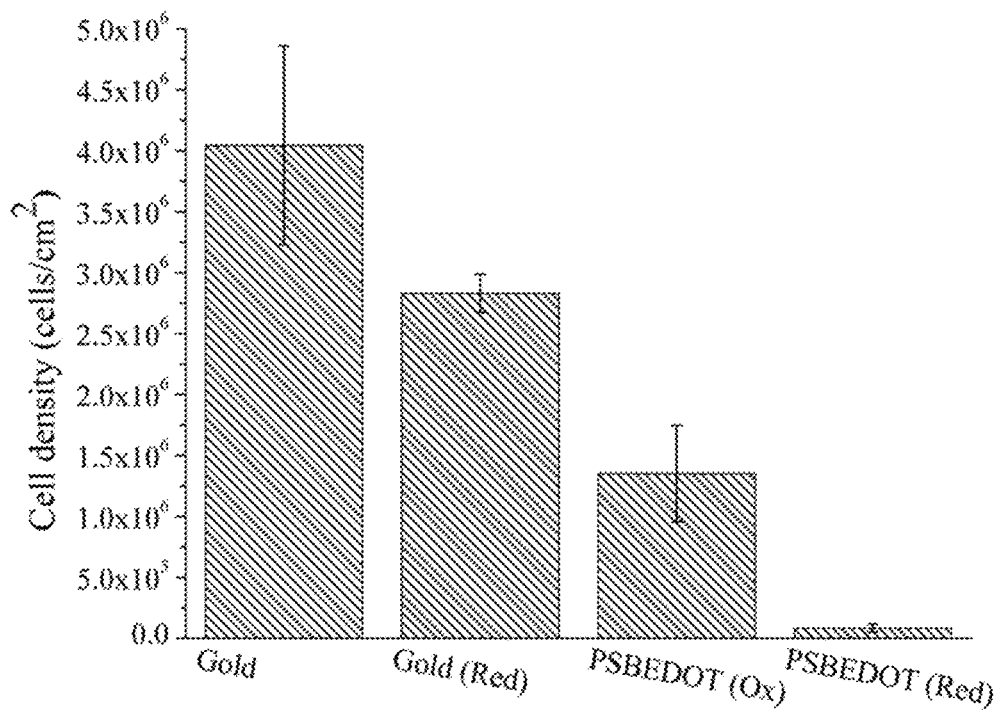
FIG. 1C is a graph showing quantitative data on detachment of E. coli K12 from oxidized PSBEDOT and gold at 0 V for 1 hour.

Another advantage of the conjugated polymer is that their potential can be adjusted. By applying a lower potential (0 V), the oxidized cationic surface can switch to the reduced zwitterionic surface and the killed bacterial cells can be released. To confirm this, a bacterial cell detachment experiment was conducted using PSBEDOT and gold surfaces that carried killed bacterial cells from the antimicrobial study. As shown in FIG. 1C, 96.7% of cells on PSBDEOT surfaces were released within 1 hour under the static condition after changing the potential to 0 V, while only 30% of cells on gold surfaces are released. The final cell density on PSBEDOT is less than 3% of that on gold substrate. It should be noted that the release of the killed bacteria cell is critical for implanted materials, since the attached dead cell may cause the chronic inflammation and lead the failure of the implanted materials/devices. Here, it has been demonstrated that PSBEDOT surfaces could effectively resist cell attachment under the reduced state, kill the small amount of attached cells under the oxidized state and release the dead cells after switching back to the reduced state.

Numerous applications ranging from the field of solid state technology to biomedical engineering, need to use high performance CPs as the key component that determine the functions and properties of the devices, so the development of novel multifunctional CP is of greater importance. One of the most attractive features of CPs over traditional biomaterials is that they could allow the electrical stimulation of the attached tissues and cells. It is expected that the novel PSBEDOT can be used to manipulate the cell attachments through electrochemical control, also can serve as protective coating to reduce the protein adsorption and cell attachment thus prolong the lifetime of implanted devices. Although there is much work to be done to fully understand and realize the potential of zwitterionic conjugated polymer, we believe this work fundamentally advance the development of entire research field.

These zwitterionic antifouling and conducting PSBEDOT coatings can be facilely formed in the aqueous solution through standard electrochemical methods. These polymer films exhibit excellent conducting properties, low interfacial impedance, stability and switchable antifouling/antimicrobial properties. The interfacial impedance of PSBEDOT is less than 10% of bare gold at low frequency. It also show superior antifouling property against single protein, whole blood, mammalian cells and bacteria. PSBEDOT surfaces can also switch between cationic antimicrobial and zwitterionic antifouling surfaces by applying different potentials.

It can kill the attached over 89% of attached cells in one hour at 0.6 V and release over 96.7% of dead cells in one hour at 0 V under static condition. It shows great promises for applications in bioelectronics. This new materials may significantly increase the performance and service life, minimize foreign body reaction, improve biocompatibility and reduce the infection of the bioelectronic devices.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Chemicals and General Instrumentation 3,4-dimethoxythiophene was purchased from Matrix Scientific (Columbia, S.C., USA). (±)-3-chloro-1,2-propanediol, toluene, p-Toluenesulfonic acid monohydrate, dimethylamine solution (40 wt. % in $H_2O$), acetonitrile, 1,3-propanesultone, anhydrous magnesium sulfate, anhydrous tetrahydrofuran (THF), chloroform, methanol, dichloromethane, ethyl acetate, phosphate-buffered saline (PBS) and fluorescein diacetate were purchased from Sigma-Aldrich (St. Louis, Mo., USA). All chemicals were used as received without further purification. Bovine aorta endothelial cell (BAEC) and Mouse NIH 3T3 fibroblast cell were purchased from American Type Culture Collection (Manassas, Md., USA). Dulbecco's Modified Eagle's Medium (DMEM) was purchased from Life Technologies (Carlsbad, Calif., USA). Water used in all experiments was purified using a Millipore Milli-Q Direct 8 Ultrapure Water system (Billerica, Mass., USA). Electro-polymerization and other electrochemical characterizations were performed on a Solartron Modulab XM ECS test system or a Gamry Reference 600 potentiostat. XPS spectra were obtained from a PHI VersaProbe II Scanning XPS Microprobe. All NMR experiments were performed at 303.2 K unless stated otherwise and on Varian Mercury 300 MHz spectrometers.

Example 1

Synthesis of Chloromethyl-EDOT

Chloromethyl-EDOT was synthesized from 3,4-dimethoxythiophene following a method set forth in J. L. Segura, R. Gomez, R. Blanco, E. Reinold and P. Bauerle, Chem Mater, 2006, 18, 2834-2847, the disclosure of which is incorporated herein by reference in its entirety. EDOT-dimethylamine was synthesized as a versatile intermediate, which was used to synthesize zwitterionic EDOT derivatives bearing carboxybetaine or sulfobetaine side chains. Chloromethyl-EDOT is also commercially available from a variety of sources including Sigma Aldrich (St Louis, Mo.).

Example 2

Synthesis of EDOT-dimethylamine (EDOT-DMA)

Chloromethyl-EDOT (3.8 g, 20 mmol) was added to a solution of dimethylamine (40 wt. % in $H_2O$) (22.5 mL, 200 mmol) and acetonitrile (22.5 mL). The mixture was sealed in a schlenk flask and heated at 80° C. for 2 days. Another 22.5 mL of dimethylamine (40 wt. % in $H_2O$) was added after it cooled down. Then the solution was heated at 80° C. for another 36 hours. After the solution cooled to room temperature, it was concentrated with a rotary evaporator, extracted with ether, dried with $MgSO_4$. Product was purified with silica gel column chromatography (MeOH/$CH_2Cl_2$/ethyl acetate, 1/10/10 (v/v/v)). Pure product was obtained as a light yellowish liquid (Yield: 65%). $^1H$ NMR (300 MHz, $CDCl_3$) δ 6.30-6.36 (m, 2H), 4.20-4.30 (m, 2H), 3.90-3.97 (m, 1H), 2.41-2.64 (m, 2H), 2.31 (s, 6H). $^{13}C$ NMR (75 MHz, CDCl3) δ 141.84, 99.90, 99.55, 71.95, 67.52, 59.65 (one carbon not seen due to overlapping signal) (See FIGS. 6, 7)

Example 3

Synthesis of SBEDOT 1,3-Propanesultone (1.46 g, 12 mmol) was slowly added into a solution of EDOT-dimethylamine (2.0 g, 10 mmol) in 50 mL of anhydrous THF. The mixture was heated at 55° C. for 36 hours under a positive nitrogen flow. After filtration, it was washed with THF and vacuum dried. The pure product was obtained as a white powder (Yield: 82%). $^1H$ NMR (300 MHz, $D_2O$) δ 6.58-6.65 (m, 2H), 5.00 (m, 1H), 4.14-4.31 (m, 2H), 3.62-3.85 (m, 4H), 3.27 (s, 3H), 3.25 (s, 3H), 2.98 (t, 2H, J=7.2 Hz), 2.22 (m, 2H). $^{13}C$ NMR (75 MHz, D2O) δ 139.94, 138.45, 101.66, 101.00, 67.80, 65.90, 63.69, 62.55, 51.97, 51.69, 47.16 See FIGS. 8, 9.

Example 4

Electropolymerization of SBEDOT

Figure 10:
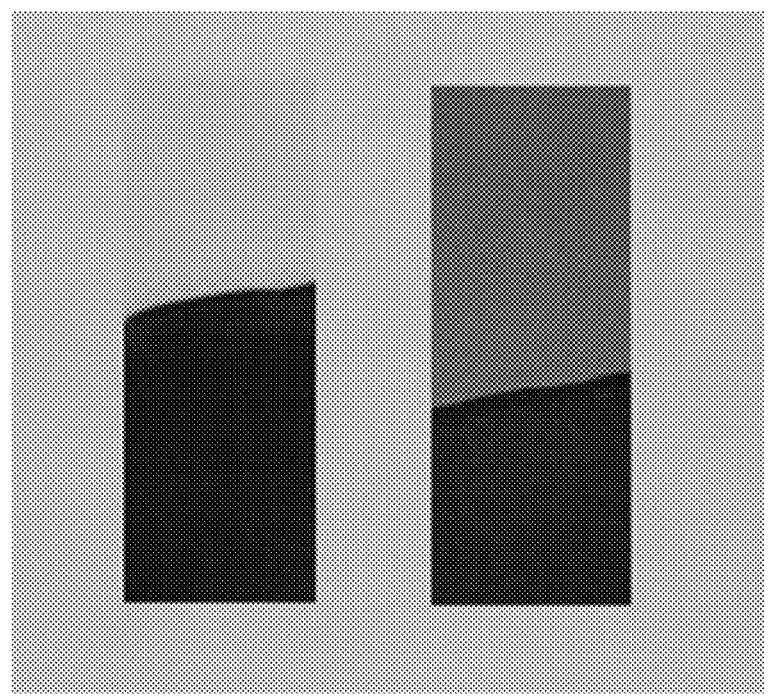
FIG. 10 is an optical images of PSBEDOT coatings according to one or more embodiments of the present invention on ITO (left) and gold (right) substrates.

Electropolymerization was performed on a Solartron Modulab XM ECS test system or a Gamry Reference 600 potentiostat equipped with a three-electrode electrochemical set-up, using a Pt electrode as the counter electrode and an Hg/$HgCl_2$ electrode (sat. KCl) as the reference electrode. One of the great advantages of this SBEDOT monomer is it could be directly polymerized in aqueous solution, which significantly facilitates its future applications in vivo. SBEDOT was polymerized on either ITO coated PET films or gold coated SPR sensor chips (See FIG. 10), with cyclic voltammetry from −0.6 V to 1.3 V, or galvanostatic method at 0.1 mA/s, from an aqueous solution containing 60 mM monomer and 100 mM $LiClO_4$ as electrolyte.

Example 5

X-Ray Photoelectron Spectroscopy (XPS) Study

XPS was also used to examine the composition profile of electropolymerized PSBEDOT film, using a PHI VersaProbe II Scanning XPS Microprobe. All data processing was performed using the software provided with the instrument.

Figure 11A:
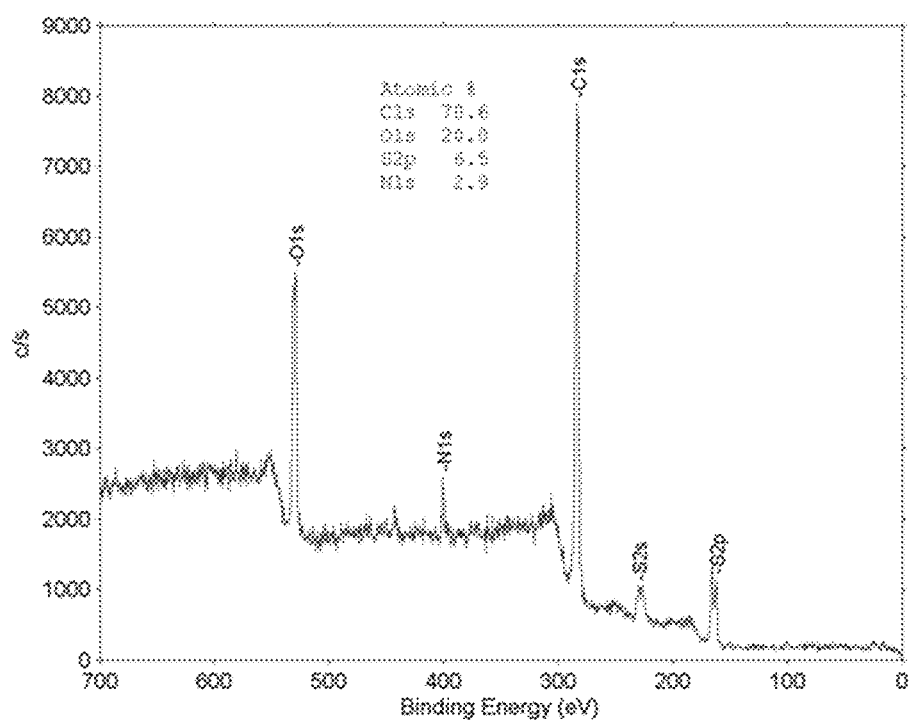

The PSBEDOT samples were run for both the survey and the high resolution spectra. The survey spectra of a PEDOT sample was used for comparison. All data processing was performed using the software provided with the instrument. Peak areas, line shapes, and intensities of C 1s, O 1s, N 1s and S 2p high resolution spectra were monitored. As shown in FIGS. 11A-B, the atomic ratios were in agreement with molecular compositions. From the S 2p high resolution spectra of PSBEDOT, two types of S were observed with equivalent peak intensity, indicating its elemental and chemical composition was exactly the same as expected. See FIG. 11A-B

Example 6

Electrochemical Characterization of PSBEDOT

Electrochemical impedance spectroscopy (EIS) and Cyclic Voltammetry (CV) were performed using a Gamry Reference 600 potentiostat in PBS buffer. Stability measurement of PSBEDOT film was carried out with CV (−0.3 V to 0.6 V). Although PSBEDOT was hydrophilic, it showed excellent stability in aqueous solution, even after applying a potential sweep for over 500 cycles (FIG. 2A). The PSBEDOT films for measurements were coated on gold coated SPR sensor chips. For EIS, the frequencies were spaced from 10 kHz to 1 Hz with a low amplitude voltage (~10 mV). Before EIS experiment, samples were equilibrated in PBS buffer for 10 minutes.

Example 7

BAECs and NIH3T3 Cell Adhesion Study

Bovine aorta endothelial cell (BAEC) and NIH3T3 were purchased from American Type Culture Collection (Manassas, Md., USA). Cell attachment study was carried out following a similar procedure to that used in a previous work (See, Cao, B.; Li, L. L.; Wu, H. Y.; Qiong, T.; Sun, B. B.; Doug, H.; Zhe, J.; Cheng, G., *Zwitteration of dextran; a facile route to integrate antifouling, switchability and optical transparency into natural polymers*, Chemical Communications 2014, 50 (24), 3234-3237, the disclosure of which is incorporated herein by reference in its entirety). PSBEDOT and PEDOT was electro-deposited on ITO coated PET substrates, then equilibrated in DI-water for 24 hours and transferred to sterilized PBS. All samples were exposed under UV for half an hour before the cell adhesion experiment.

BAECs and NIH3T3 were separately seeded on different substrates at $10^5$ cells/mL with DMEM medium consisting of DMEM, 10% fetal bovine serum (FBS), and 1% penicillin-streptomycin and kept in an incubator with 5% $CO_2$ at 37° C. for 24 hours. After the incubation, medium was removed from the wells. After very gently rinsing with sterilized PBS, the substrate was changed to a staining solution that was prepared in sterilized PBS as follows. Fluorescein diacetate was dissolved at a concentration of 10 mg $mL^{-1}$ in acetone. 50 μL of that solution was then diluted in 10 mL sterilized PBS and used for staining the cells. After the substrates were incubated for 5 min with the staining solution, surface cell coverage and cell morphology was visualized and imaged with an Olympus IX81 fluorescence microscope (Olympus, Japan) equipped with a FITC filter at 4× or 10× magnification. See FIG. 4A-C and Table 1, above.

Example 8

Protein Adsorption Studies

1. SPR Study

A surface plasmon resonance sensor SPR sensor was used to measure protein adsorption on PSBEDOT surface. First, a PBS solution at a 50 μL $min^{-1}$ flow rate was used to obtain a baseline signal. Then, 100% human blood plasma and 30% diluted human blood serum were then injected into different channels for 10 minutes followed by a PBS wash to remove any loosely bound proteins. The amount of adsorbed proteins was calculated as the change in wavelength before and after protein injection.

2. Surface Adsorption of FITC-Labeled Fibrinogen

Figure 12A:
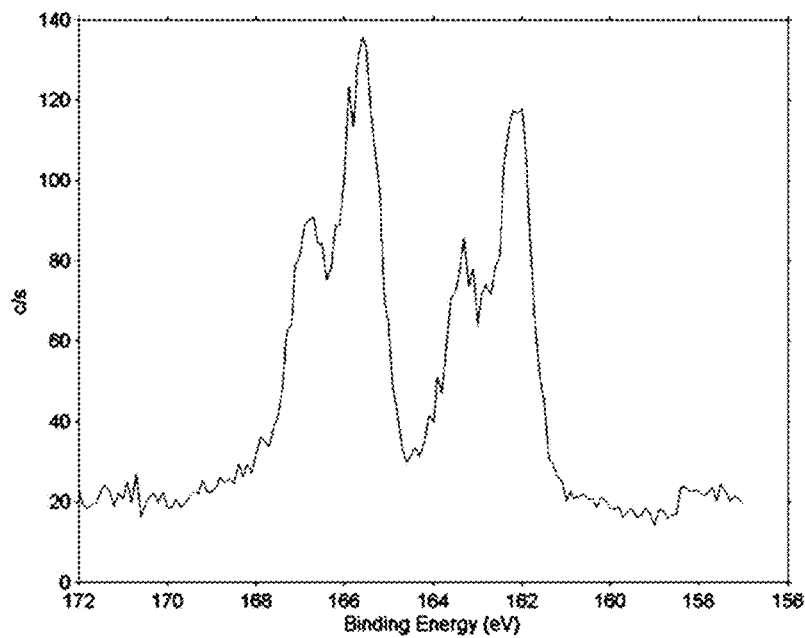
FIG. 12A-C are images showing the results of a protein (FITC-Fg) adsorption test on surfaces visualized under fluorescence microscope at the same excitation light intensity and exposure time.
Figure 12A:
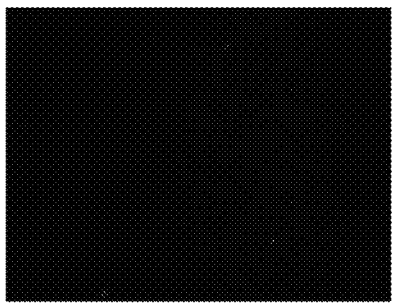
Figure 12B:
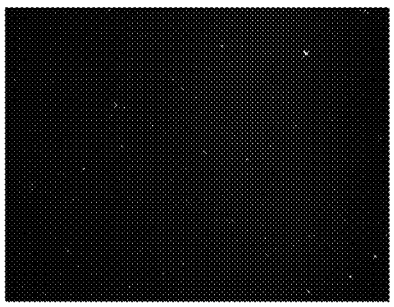
Figure 12C:
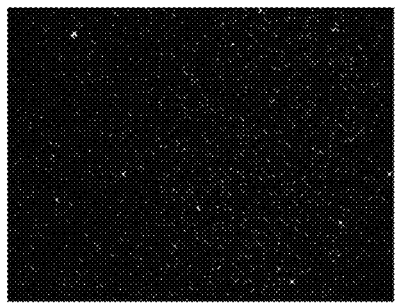

After equilibrated in PBS, the substrates was gently rinsed with DI-water and then transferred into a sterile 12-well plate. 4 mL of FITC-labelled fibrinogen (FITC-Fg) solution (0.1 mg/mL) was added into each well. All samples were immersed in the solution for 30 minutes to allow protein adsorption on substrate surfaces. To remove loosely adsorbed proteins on sample surfaces, all samples were gently rinsed with PBS. Protein adsorption on each substrate surface was visualized with an Olympus IX81 fluorescent microscopy (Olympus, Japan) with 4× objective lens through FITC filter at a fixed exposure time for all samples, so the different protein adsorption will lead to different fluorescent intensity on images. ImageJ software was used to quantify the fluorescent intensity of each sample. The results are shown in FIGS. 4A-C. See also, FIG. 12A-C.

Example 9

Bacterial Adhesion, Antimicrobial and Releasing Studies

The method for evaluating the antibacterial efficiency of polymer surfaces was modified from a previously published method. (See, J. C. Tiller, C. J. Liao, K. Lewis and A. M. Klibanov, *Proceedings of the National Academy of Sciences of the United States of America*, 2001, 98, 5981-5985, the disclosure of which is encorporated herein by reference in its entirety.) *E. coli* K12 was first cultured in separate pure cultures overnight at 37° C. on Luria-Bertani (LB) agar plates. One colony was used to inoculate 5 mL of LB medium (20 g/L). These initial cultures were incubated at 37° C. with shaking at 200 rpm for 12 hours. This culture was then used to inoculate a second culture in 25 mL of LB medium. When the second suspended culture reached an optical density of 0.8 at 600 nm, bacteria were collected by centrifugation at 8,000×g for 10 min at 4° C. Cell pellets were washed three times with sterile PBS (pH 7.4) and subsequently suspended in PBS to get a final concentration of $10^9$ cells/mL.

1. Bacterial Attachment Study

Before the bacterial attachment study, PSBEDOT coated Au substrates was equilibrated under 0.6 V and 0 V in PBS for 20 minutes to obtain surface at the oxidized state and reduced state respectively. A 0.1 mL suspension of *E. coli* at a concentration of $10^9$ cells/mL was pipetted onto each PSBEDOT coated Au substrate and then covered with a glass cover slip. The sample was incubated at room temperature for 1 hour. The cover slide was removed and the sample was rinsed in 50 mL of PBS. Then, the sample in PBS was stained with 1 mL of water containing 20 μM of red fluorescent nucleic acid stain propidium iodide (Life Technologies, Carlsbad, Calif.). The number of cells was determined with a CCD-CoolSNAP camera (Roper scientific, Inc., USA) mounted on Olympus IX81 fluorescent microscopy (Olympus, Japan) with 40× objective lens through FITC filter. Three separate samples were analyzed for each coating. See, FIGS. 1A-C.

2. Antimicrobial Study

After the cell attachment study, same PSBEDOT substrates with attached cells were transferred to PBS solution and 0.6 V potential was applied for 1 h. The sample was rinsed in 50 mL of PBS. Then, the sample in PBS was stained with 1 mL of water containing 20 μM of red fluorescent nucleic acid stain propidium iodide and 3.34 μM green fluorescent nucleic acid stain SYTO9 (Life Technologies, Carlsbad, Calif.). The number of live and dead cells was determined with a CCD-CoolSNAP camera (Roper scientific, Inc., USA) mounted on Olympus IX81 fluorescent microscopy (Olympus, Japan) with 40× objective lens through FITC filter and Texas Red filter at a fixed exposure time for all samples. Three separate samples were analyzed for each coating. See, FIG. 1B.

3. Bacterial Release Study

After the antimicrobial study, same PSBEDOT substrates with attached cells were transferred to PBS solution and 0 V potential was applied for 1 h. The sample was rinsed in 50 mL of PBS. The number of live and dead cells was determined with a CCD-CoolSNAP camera (Roper scientific, Inc., USA) mounted on Olympus IX81 fluorescent microscopy (Olympus, Japan) with 40× objective lens through FITC filter and Texas Red filter at a fixed exposure time for all samples. Three separate samples were analyzed for each coating. See, FIG. 1C In light of the foregoing, it should be appreciated that the present invention significantly advances the art by providing a novel method for forming a conjugated polymer film on a substrate that is improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A method of forming a polymer film or coating on a substrate from an aqueous solution of one or more hydrophilic 3 4-ethylenedioxythiophene (EDOT)-derived monomer(s) comprising:
   A. selecting a suitable substrate, said substrate having a conductive or semiconductive surface;
   B. preparing a hydrophilic EDOT monomer comprising a terminal EDOT group and a betaine group;
   C. dissolving said hydrophilic EDOT monomer in water or an aqueous solution;
   D. placing said substrate in the solution of step C so that the solution of step C is in contact with the surface of said substrate;
   E. applying an electric current to the solution of step C, thereby causing said hydrophilic EDOT monomer to polymerize on the surface of said substrate.

2. The method of claim 1 wherein said substrate is selected from the group consisting of implantable medical devices, steel, stainless steel, titanium, titanium alloys, silicon, and/or ITO coated substrates, gold coated substrates, aluminum, aluminum alloys, platinum, noble metals, and alloys and combinations thereof.

3. The method of claim 1 wherein said conductive or semiconductive surface comprises a conductive or semiconductive material selected from the group consisting of steel, stainless steel, titanium, titanium alloys, aluminum, aluminum alloys, silicon, iridium tin oxide (ITO), gold, platinum, noble metals, and alloys and combinations thereof.

4. The method of claim 1 wherein said betaine group is a sulfobetaine.

5. The method of claim 1 wherein the hydrophilic EDOT monomer is 3-(((2,3-dihydrothieno[3,4-b][1,4]dioxin-2-yl)methyl)dimethylammonio)propane-1-sulfonate.

6. The method of claim 1 wherein the hydrophilic EDOT monomer has the formula:

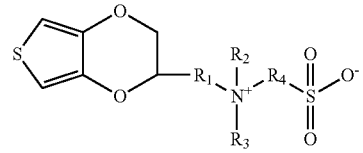

wherein $R_1$ is —$CH_2$—, —$CH_2CH_2$—, —$CH_2CH_2CH_2$—, —$CH_2CH_2CH_2CH_2$—, —$CH_2CH_2CH_2CH_2CH_2$—, —$(CH_2)_m$— or —$(CH_2)_yO(CH_2)_x$—; $R_2$ is —H, —$CH_3$, —$CH_2CH_3$, —$CH_2CH_2CH_3$, —$CH_2CH_2CH_2CH_3$, —$CH_2CH_2OH$, —$CH_2CH_2CH_2OH$, —$CH_2CH_2CH_2CH_2OH$, or —$CH_2CH_2CH_2CH_2CH_2OH$; $R_3$ is —H, —$CH_3$, —$CH_2CH_3$, —$CH_2CH_2CH_3$, —$CH_2CH_2CH_2CH_3$, —$CH_2CH_2OH$, —$CH_2CH_2CH_2OH$, —$CH_2CH_2CH_2CH_2OH$, or —$CH_2CH_2CH_2CH_2CH_2OH$; and $R_4$ is —$CH_2$—, —$CH_2CH_2$—, —$CH_2CH_2CH_2$—, —$CH_2CH_2CH_2CH_2$—, —$CH_2CH_2CH_2CH_2CH_2$—, —$(CH_2)_x$—, or —$(CH_2)_vO(CH_2)_w$—; and m, x, y, v and w are each an integer from 1 to 20.

7. The method of claim 1 wherein the hydrophilic EDOT monomer has a formula selected from the group consisting of:

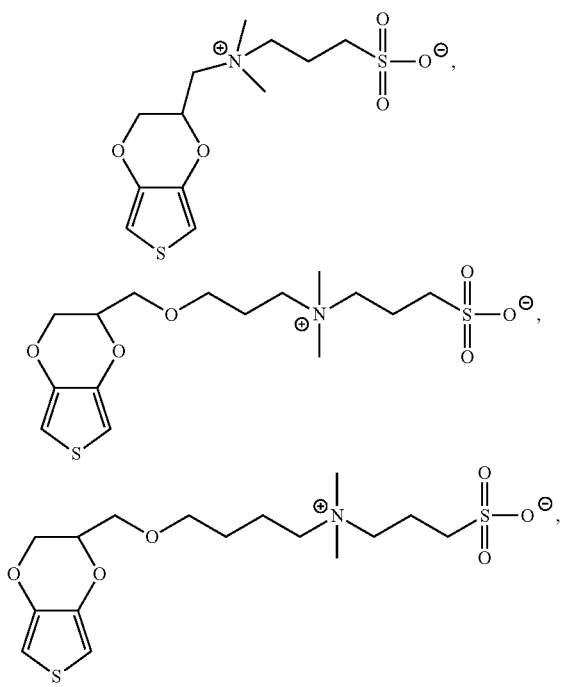

-continued

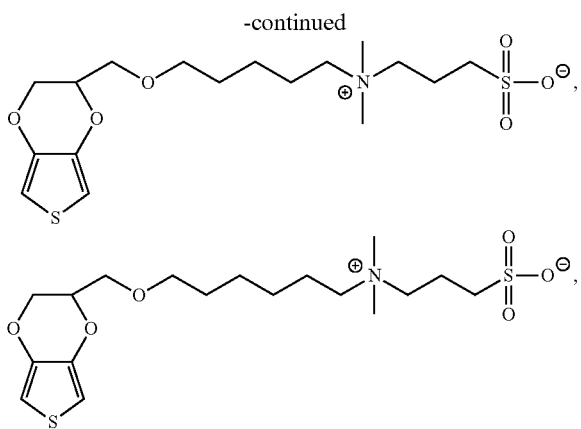

and combinations thereof.

8. The method of claim 1 wherein the hydrophilic EDOT monomer is zwitterionic.

9. The method of claim 1 wherein the concentration of hydrophilic EDOT monomer in the solution of step C is from about 0.001 mM to about 1000 mM.

10. The method of claim 1 wherein said the solution of step C further comprises an electrolyte selected from the group consisting of $LiClO_4$, NaCl, KCl, $Na_2HPO_4$, $NaH_2PO_4$, $CaCl_2$, $MgCl_2$, $CaSO_4$, $MgSO_4$, and combinations thereof.

11. The method of claim 10 wherein the concentration of said electrolyte in the solution of step C is from about 0.1 mM to about 1000 mM.

12. The method of claim 1 wherein the step of applying an electric current further comprises applying a cyclic voltage of from −0.6 V to 1.3 V.

13. The method of claim 1 wherein the step of applying an electric current comprises applying a current having a current density of 0.01 $mA/cm^2$ to 100 $mA/cm^2$.

14. A PSBEDOT polymer coating made using the method of claim 1.

15. The PSBEDOT polymer coating of claim 14 wherein said PSBEDOT polymer coating has a cationic (oxidized) state and a zwitterionic (reduced) state.

16. The PSBEDOT polymer coating of claim 14 having an interfacial impedance that is less than 60% of the surface to which it is applied.

17. The PSBEDOT polymer coating of claim 14 having a protein adsorption of from 200 $ng/cm^2$ to 0.001 $ng/cm^2$ in human blood plasma in its reduced state.

18. The PSBEDOT polymer coating of claim 14 having a protein adsorption of from 200 $ng/cm^2$ to 0.001 $ng/cm^2$ in 30% human blood serum in its reduced state.

* * * * *